(12) United States Patent
Raab et al.

(10) Patent No.: US 9,051,587 B2
(45) Date of Patent: Jun. 9, 2015

(54) YEAST CELL FOR THE PRODUCTION OF TERPENES AND USES THEREOF

(75) Inventors: Andreas Raab, Berlin (DE); Christine Lang, Berlin (DE)

(73) Assignee: OrganoBalance GmbH, Berlin (DE)

( * ) Notice: Subject to any disclaimer, the term of this patent is extended or adjusted under 35 U.S.C. 154(b) by 48 days.

(21) Appl. No.: 13/984,761

(22) PCT Filed: Feb. 15, 2012

(86) PCT No.: PCT/EP2012/000665
§ 371 (c)(1),
(2), (4) Date: Oct. 17, 2013

(87) PCT Pub. No.: WO2012/116783
PCT Pub. Date: Sep. 7, 2012

(65) Prior Publication Data
US 2014/0057328 A1  Feb. 27, 2014

(30) Foreign Application Priority Data
Feb. 28, 2011 (EP) .................................... 11001629

(51) Int. Cl.
| | | |
|---|---|---|
| C12P 5/02 | (2006.01) | |
| C12N 9/02 | (2006.01) | |
| C12N 9/04 | (2006.01) | |
| C12N 9/10 | (2006.01) | |
| C12N 15/81 | (2006.01) | |

(52) U.S. Cl.
CPC ............. *C12P 5/026* (2013.01); *C12N 9/0004* (2013.01); *C12N 9/0006* (2013.01); *C12N 9/1025* (2013.01); *C12P 5/02* (2013.01); *C12N 15/81* (2013.01)

(58) Field of Classification Search
None
See application file for complete search history.

(56) References Cited

FOREIGN PATENT DOCUMENTS

EP  0486290 A2  5/1992

OTHER PUBLICATIONS

Polakowski et al., "Overexpression of a cytosolic hydroxymethylglutaryl-CoA reductase leads to squalene accumulation in yeast," Appl Microbiol Biotechnol. 49:66-71 (1998).
Raab et al., "Innovatives Verfahren zur Herstellung von Squalen mit Hefe," http://www.dbu.de/OPAC/ab/DBU-Abschlussbericht-AZ-13202.pdf. Retrieved on Aug. 7, 2013 (34 pages).
Sikorski et al., "A system of shuttle vectors and yeast host strains designed for efficient manipulation of DNA in *Saccharomyces cerevisiae*," Genetics. 122:19-27 (1989).
International Search Report and Written Opinion for International Patent Application No. PCT/EP2012/000665, mailed Aug. 24, 2012 (12 pages).
Basson et al, "Structural and functional conservation between yeast and human 3-hydroxy-3-methylglutaryl coenzyme A reductases, the rate-limiting enzyme of sterol biosynthesis," Mol Cell Biol. 8:3797-808 (1988).
Boeke et al., "5-Fluoroorotic acid as a selective agent in yeast molecular genetics," Methods Enzymol. 154:164-75 (1987).
Bennetzen et al., "The primary structure of the *Saccharomyces cerevisiae* gene for alcohol dehydrogenase I*" J. of Biol. Chem. 257:3018-25 (1982).
Berben et al., "The Ydp plasmids: a uniform set of vectors bearing versatile gene disruption cassettes for *Saccharomyces cerevisiae*," Yeast. 7:475-77 (1991).
Gietz et al., "Improved method for high efficiency transformation of intact yeast cells," Nucleic Acids Res. 20:1425 (1992).
Gaber et al., "Frameshift suppression in *Saccharomyces Cerevisiae* IV. New suppressors among spontaneous co-revertants of the group II HIS4-206 and LEU2-3 frameshift mutations," Genetics. 101:345-67 (1982).
Ebright et al., "Short Communications: Corrected nucleotide sequence of M13mp18 gene III," Gene. 114:81-83 (1992).
Guldener et al., "A new efficient gene disruption cassette for repeated use in budding yeast," Nucleic Acids Res. 24:2519-24 (1996).
Hinnen et al., "Transformation of yeast," Proc Natl Acad Sci USA. 75:1929-33 (1978).
Lang et al., "Efficient expression and secretion of *Aspergillus niger* RH5344 polygalacturonase in *Saccharomyces cerevisiae*," Appl Microbiol Biotechnol. 44:147-56 (1995).
Mortimer et al., "Genealogy of principal strains of the yeast genetic stock center," Genetics. 113:35-43 1986.
Parent et al., "Vector systems for the expression, analysis and cloning of DNA sequences in *S. cerevisiae*," Yeast. 1:83-138 (1985).
Pronk, "Auxotrophic yeast strains in fundamental and applied research," Appl Environ Microbiol. 68:2095-100 (2002).
Tschumper et al., "Sequence of a yeast DNA fragment containing a chromosomal replicator and the TRP1 gene," Gene. 10:157-66 (1980).
Webster et al., "Direct selection of *Saccharomyces cerevisiae* resistant to the antibiotic G418 following transformation with a DNA vector carrying the kanamycin-resistance gene of Tn903," Gene. 26:243-52(1983).
Yanisch-Perron et al., "Improved M13 phage cloning vectors and host strains: nucleotide sequences of the M13mp18 and pUC19 vectors," Gene. 33:103-19 (1985).

*Primary Examiner* — Suzanne M Noakes
(74) *Attorney, Agent, or Firm* — Clark & Elbing LLP

(57) ABSTRACT

The present invention relates to a yeast cell, wherein said cell comprises a functional gene coding for soluble hydroxymethylglutaryl-coenzyme-A (HMG-CoA) reductase; one or more gene(s) coding for steryl acyltransferase(s) in said cell are defective or deleted; and said cell is prototrophic for at least histidine, leucine or uracil. Moreover, the present invention relates to the use of said cell for the production of one or more terpene(s). Further, the present invention relates to methods of generating said cell and the production of one or more terperne(s) and a pharmaceutical or cosmetically composition, a lubricant or transformer oil comprising said terpene(s).

16 Claims, 8 Drawing Sheets

SEQUENCE LISTING

```
<160> NUMBER OF SEQ ID NOS: 7

<210> SEQ ID NO 1
<211> LENGTH: 1578
<212> TYPE: DNA
<213> ORGANISM: Artificial Sequence
<220> FEATURE:
<223> OTHER INFORMATION: truncated HMG CoA reductase

<400> SEQUENCE: 1
atggaccaat tggtgaaaac tgaagtcacc aagaagtctt ttactgctcc tgtacaaaag      60
gcttctacac cagttttaac caataaaaca gtcatttctg gatcgaaagt caaaagttta    120
tcatctgcgc aatcgagctc atcaggacct tcatcatcta gtgaggaaga tgattcccgc    180
gatattgaaa gcttggataa gaaaatacgt cctttagaag aattagaagc attattaagt    240
agtggaaata caaacaatt gaagaacaaa gaggtcgctg ccttggttat tcacggtaag    300
ttacctttgt acgctttgga gaaaaaatta ggtgatacta cgagagcggt tgcggtacgt    360
aggaaggctc tttcaatttt ggcagaagct cctgtattag catctgatcg tttaccatat    420
aaaaattatg actacgaccg cgtatttggc gcttgttgtg aaaatgttat aggttacatg    480
cctttgcccg ttggtgttat aggccccttg gttatcgatg gtacatctta tcatatacca    540
atggcaacta cagagggttg tttggtagct tctgccatgc gtggctgtaa ggcaatcaat    600
gctggcggtg gtgcaacaac tgtttttaact aaggatggta tgacaagagg cccagtagtc    660
cgtttcccaa ctttgaaaag atctggtgcc tgtaagatat ggttagactc agaagaggga    720
caaaacgcaa ttaaaaaagc ttttaactct acatcaagat ttgcacgtct gcaacatatt    780
caaacttgtc tagcaggaga tttactcttc atgagattta gaacaactac tggtgacgca    840
atgggtatga atatgatttc taaaggtgtc gaatactcat taaagcaaat ggtagaagag    900
tatggctggg aagatatgga ggttgtctcc gtttctggta actactgtac cgacaaaaaa    960
ccagctgcca tcaactggat cgaaggtcgt ggtaagagtg tcgtcgcaga agctactatt   1020
cctggtgatg ttgtcagaaa agtgttaaaa agtgatgttt ccgcattggt tgagttgaac   1080
attgctaaga atttggttgg atctgcaatg gctgggtctg ttggtggatt taacgcacat   1140
gcagctaatt tagtgacagc tgttttcttg gcattaggac aagatcctgc acaaaatgtt   1200
gaaagttcca actgtataac attgatgaaa gaagtggacg tgatttgag aatttccgta   1260 tccatgccat ccatcgaagt aggtaccatc ggtggtggta ctgttctaga accacaaggt   1320
gccatgttgg acttattagg tgtaagaggc ccgcatgcta ccgctcctgg taccaacgca   1380
cgtcaattag caagaatagt tgcctgtgcc gtcttggcag gtgaattatc cttatgtgct   1440
gccctagcag ccggccattt ggttcaaagt catatgaccc acaacaggaa acctgctgaa   1500
ccaacaaaac ctaacaattt ggacgccact gatataaatc gtttgaaaga tgggtccgtc   1560
acctgcatta aatcctaa                                                  1578
```

<210> SEQ ID NO 2
<211> LENGTH: 1635
<212> TYPE: DNA
<213> ORGANISM: Artificial Sequence
<220> FEATURE:
<223> OTHER INFORMATION: based on vector pUC19

<400> SEQUENCE: 2

```
actatggacc aattggtgaa aactgaagtc accaagaagt cttttactgc tcctgtacaa      60
aaggcttcta caccagtttt aaccaataaa acagtcattt ctggatcgaa agtcaaaagt     120
ttatcatctg cgcaatcgag ctcatcagga ccttcatcat ctagtgagga agatgattcc     180
cgcgatattg aaagcttgga taagaaaata cgtcctttag aagaattaga agcattatta     240
agtagtggaa atacaaaaca attgaagaac aaagaggtcg ctgccttggt tattcacggt     300
aagttacctt tgtacgcttt ggagaaaaaa ttaggtgata ctacgagagc ggttgcggta     360
cgtaggaagg ctctttcaat tttggcagaa gctcctgtat tagcatctga tcgtttacca     420
tataaaaatt atgactacga ccgcgtattt ggcgcttgtt gtgaaaatgt tataggttac     480
atgcctttgc ccgttggtgt tataggcccc ttggttatcg atggtacatc ttatcatata     540
ccaatggcaa ctacagaggg ttgtttggta gcttctgcca tgcgtggctg taaggcaatc     600
aatgctggcg gtggtgcaac aactgtttta actaaggatg gtatgacaag aggcccagta     660
gtccgtttcc caactttgaa aagatctggt gcctgtaaga tatggttaga ctcagaagag     720
ggacaaaacg caattaaaaa agcttttaac tctacatcaa gatttgcacg tctgcaacat     780
attcaaactt gtctagcagg agatttactc ttcatgagat ttagaacaac tactggtgac     840
gcaatgggta tgaatatgat ttctaaaggt gtcgaatact cattaaagca aatggtagaa     900
gagtatggct gggaagatat ggaggttgtc tccgtttctg gtaactactg taccgacaaa     960
aaaccagctg ccatcaactg gatcgaaggt cgtggtaaga gtgtcgtcgc agaagctact    1020
attcctggtg atgttgtcag aaaagtgtta aaaagtgatg tttccgcatt ggttgagttg    1080
aacattgcta gaatttggt tggatctgca atggctgggt ctgttggtgg atttaacgca    1140
catgcagcta atttagtgac agctgttttc ttggcattag acaagatccc tgcacaaaat    1200
gttgaaagtt ccaactgtat aacattgatg aaagaagtgg acggtgattt gagaatttcc    1260
gtatccatgc catccatcga agtaggtacc atcggtggtg gtactgttct agaaccacaa    1320
ggtgccatgt tggacttatt aggtgtaaga ggcccgcatg ctaccgctcc tggtaccaac    1380
gcacgtcaat tagcaagaat agttgcctgt gccgtcttgg caggtgaatt atccttatgt    1440
gctgccctag cagccggcca tttggttcaa agtcatatga cccacaacag gaaacctgct    1500
gaaccaacaa aacctaacaa tttggacgcc actgatataa atcgtttgaa agatgggtcc    1560
gtcacctgca ttaaatccta atagtcatac gtcattggta ttctcttgaa aaagaagcac    1620
aacagcacca tgtgt                                                    1635
```

<210> SEQ ID NO 3
<211> LENGTH: 4820
<212> TYPE: DNA
<213> ORGANISM: Artificial Sequence
<220> FEATURE:
<223> OTHER INFORMATION: expression cassette integrated into URA3 locus

<400> SEQUENCE: 3

```
atgtcgaaag ctacatataa ggaacgtgct gctactcatc ctagtcctgt tgctgccaag      60
```

```
ctatttaata tcatgcacga aaagcaaaca aacttgtgtg cttcattgga tgttcgtacc      120
accaaggaat tactggagtt agttgaagca ttaggtccca aaatttgttt actaaaaaca      180
catgtggata tcttgactga ttttccatg gagggcacag ttaagccgct aaaggcatta       240
tccgccaagt acaattttt actcttcgaa gacagaaaat ttgctgacat tggtaataca       300
gtcaaattgc agtactctgc gggtgtatac agaatagcag aatgggcaga cattacgaat      360
gcacacggtg tggtgggccc aggtattgtt agcggtttga agcaggcggc agaagaagta      420
acaaaggaac ctagaggcga acgccagcaa gacgtagccc agcgcgtcgg ccgccatgcc      480
ggcgataatg gcctgcttct cgccgaaacg tttggtggcg ggaccagtga cgaaggcttg      540
agcgagggcg tgcaagattc gaataccgc aagcgacagg ccgatcatcg tcgcgctcca      600
gcgaaagcgg tcctcgccga aaatgaccca gagcgctgcc ggcacctgtc ctacgagttg      660
catgataaag aagacagtca taagtgcggc gacgatagtc atgccccgcg cccaccggaa      720
ggagctgact gggttgaagg ctctcaaggg catcggtcga cgctctccct tatgcgactc      780
ctgcattagg aagcagccca gtagtaggtt gaggccgttg agcaccgccg ccgcaaggaa      840
tggtgcgaac gccagcaaga cgtagcccag cgcgtcggcc gccatgccgg cgataatggc      900
ctgcttctcg ccgaaacgtt tggtggcggg accagtgacg aaggcttgag cgagggcgtg      960
caagattccg aataccgcaa gcgacaggcc gatcatcgtc gcgctccagc gaaagcggtc      1020
ctcgccgaaa atgacccaga gcgctgccgg cacctgtcct acgagttgca tgataaagaa      1080
gacagtcata agtgcggcga cgatagtcat gccccgcgcc caccggaagg agctgactgg      1140
gttgaaggct ctcaagggca tcggtcgacg ctctcctta tgcgactcct gcattaggaa       1200
gcagcccagt agtaggttga ggccgttgag caccgccgcc gcaaggaatg gtgcatgcaa      1260
ggagatggcg cccaacagtc ccccggccac ggggcctgcc accatacccca gccgaaaaca     1320 agcgctcatg agcccgaagt ggcgagcccg atcttcccca tcggtgatgt cggcgatata      1380
ggcgccagca accgcacctg tggcgccggt gatgccggcc acgatgcgtc cggcgtagag      1440
gatcttttat gcttgctttt caaaaggcct gcaggcaagt gcacaaacaa tacttaaata     1500
aatactactc agtaataacc tatttcttag cattttgac gaaatttgct attttgttag      1560
agtcttttac accatttgtc tccacacctc cgcttacatc aacaccaata acgccattta     1620
atctaagcgc atcaccaaca ttttctggcg tcagtccacc agctaacata aaatgtaagc     1680
ttgcatgcct gcaggtcgac tctagaggat ccccagtcac atggtgctgt tgtgcttctt     1740
tttcaagaga ataccaatga cgtatgacta agtttaggat ttaatgcagg tgacggaccc     1800
atctttcaaa cgatttatat cagtggcgtc caaattgtta ggttttgttg gttcagcagg     1860
tttcctgttg tgggtcatat gactttgaac caaatggccg gctgctaggg cagcacataa     1920
ggataattca cctgccaaga cggcacaggc aactattctt gctaattgac gtgcgttggt     1980
accaggagcg gtagcatgtg ggcctcttac acctaataag tccaacatgg caccttgtgg     2040
ttctagaaca gtaccaccac cgatggtacc tacttcgatg gatggcatgg atacggaaat     2100
tctcaaatca ccgtccactt cttccatcaa tgttatacag ttggaacttt caacattttg     2160
tgcaggatct tgtcctaatg ccaagaaaac agctgtcact aaattagctg catgtgcgtt     2220
aaatccacca acagacccag ccattgcaga tccaaccaaa ttcttagcaa tgttcaactc     2280
aaccaatgcg gaaacatcac ttttaacac ttttctgaca acatcaccag gaatagtagc      2340
ttctgcgacg acactcttac cacgaccttc gatccagttg atggcagctg gttttttgtc     2400
ggtacagtag ttaccagaaa cggagacaac ctccatatct tcccagccat actcttctac     2460
```

```
catttgcttt aatgagtatt cgacacctttt agaaatcata ttcataccca ttgcgtcacc    2520
agtagttgtt ctaaatctca tgaagagtaa atctcctgct agacaagttt gaatatgttg    2580
cagacgtgca aatcttgatg tagagttaaa agcttttttta attgcgtttt gtccctcttc    2640
tgagtctaac catatcttac aggcaccaga tcttttcaaa gttgggaaac ggactactgg    2700
gcctcttgtc ataccatcct tagttaaaac agttgttgca ccaccgccag cattgattgc    2760
cttacagcca cgcatggcag aagctaccaa acaaccctct gtagttgcca ttggtatatg    2820
ataagatgta ccatcgataa ccaaggggcc tataacacca acgggcaaag gcatgtaacc    2880
tataacattt tcacaacaag cgccaaatac gcggtcgtag tcataatttt tatatggtaa    2940
acgatcagat gctaatacag gagcttctgc caaaattgaa agagccttcc tacgtaccgc    3000
aaccgctctc gtagtatcac ctaatttttt ctccaaagcg tacaaaggta acttaccgtg    3060
aataaccaag gcagcgacct ctttgttctt caattgtttt gtatttccac tacttaataa    3120
tgcttctaat tcttctaaag gacgtatttt cttatccaag ctttcaatat cgcgggaatc    3180
atcttcctca ctagatgatg aaggtcctga tgagctcgat tgcgcagatg ataaactttt    3240
gactttcgat ccagaaatga ctgttttatt ggttaaaact ggtgtagaag cctttttgtac   3300 aggagcagta aaagacttct tggtgacttc agttttcacc atttggtcca tagtgggtac    3360
cgagctcgaa ttccttgatt gtatgcttgg tatagcttga aatattgtgc agaaaaagaa    3420
acaaggaaga aagggaacga gaacaatgac gaggaaacaa aagattaata attgcaggtc    3480
tatttatact tgatagcaag acagcaaaact ttttttttatt tcaaattcaa gtaactggaa    3540
ggaaggccgt ataccgttgc tcattaaaga gtagtgtgcg tgaatgaagg aaggaaaaag    3600
tttcgtgtgc ttcgagatac ccctcatcag ctctggaaca acgacatctg ttggtgctgt    3660
ctttgtcgtt aatttttttcc tttagtgtct tccatcatttt ttttgtcatt gcggatatgg    3720
tgagacaaca acgggggaga gagaaaagaa aaaaaaagaa aagaagttgc atgcgcctat    3780
tattacttca atagatggca aatggaaaaa gggtagtgaa acttcgatat gatgatggct    3840
atcaagtcta gggctacagt attagttcgt tatgtaccac catcaatgag gcagtgtaat    3900
tggtgtagtc ttgtttagcc cattatgtct tgtctggtat ctgttctatt gtatatctcc    3960
cctccgccac ctacatgtta gggagaccaa cgaaggtatt ataggaatcc cgatgtatgg    4020
gtttggttgc cagaaaagag gaagtccata ttgtacaccc ggaaacaaca aaaggatcaa    4080
ggagatggcg cccaacagtc ccccccggcca cggggcctgc caccataccc acgccgaaac    4140
aagcgctcat gagcccgaag tggcgagccc gatcttcccc atcggtgatg tcggcgatat    4200
aggcgccagc aaccgcacct gtggcgccgg tgatgccggc cacgatgcgt ccggcgtaga    4260
ggatccacag gacgggtgtg gtcgccatga tcgcgtagtc gatagtggct ccaagtagcg    4320
aagcgagcag gactgggcgg cggccaaagc ggtcggacag tgctccgaga acgggtgcgc    4380
atagaaattg catcaacgca tatagcgcta gcagcacgcc atagtgactg gcgatgctgt    4440
cggaatggac gatccttttg atgttagcag aattgtcatg caagggctcc ctatctactg    4500
gagaatatac taagggtact gttgacattg cgaagagcga caaagatttt gttattggct    4560
ttattgctca aagagacatg ggtggaagag atgaaggtta cgattggttg attatgacac    4620
ccggtgtggg tttagatgac aagggagacg cattgggtca acagtataga accgtggatg    4680
atgtggtctc tacaggatct gacattatta ttgttggaag aggactatttt gcaaagggaa    4740 gggatgctaa ggtagagggt gaacgttaca gaaaagcagg ctgggaagca tatttgagaa    4800
```

```
gatgcggcca gcaaaactaa                                             4820
```

<210> SEQ ID NO 4
<211> LENGTH: 1694
<212> TYPE: DNA
<213> ORGANISM: Artificial Sequence
<220> FEATURE:
<223> OTHER INFORMATION: integrative cassette used for deletion of gene
      ARE1

<400> SEQUENCE: 4

```
atgacggaga ctaaggattt gttgcaagac gaagagtttc ccagctgaag cttcgtacgc     60
tgcaggtcga caacccttaa tataacttcg tataatgtat gctatacgaa gttattaggt    120
ctagagatct gtttagcttg cctcgtcccc gccgggtcac ccggccagcg acatggaggc    180
ccagaatacc ctccttgaca gtcttgacgt gcgcagctca ggggcatgat gtgactgtcg    240
cccgtacatt tagcccatac atccccatgt ataatcattt gcatccatac attttgatgg    300
ccgcacggcg cgaagcaaaa attacggctc tcgctgcag acctgcgagc agggaaacgc     360
tccctcaca gacgcgttga attgtcccca cgccgcgccc ctgtagagaa atataaagg      420
ttaggatttg ccactgaggt tcttctttca tatacttcct tttaaaatct tgctaggata    480
cagttctcac atcacatccg aacataaaca accatgggta aggaaaagac tcacgtttcg    540
aggccgcgat taaattccaa catggatgct gatttatatg ggtataaatg gctcgcgat    600
aatgtcgggc aatcaggtgc gacaatctat cgattgtatg ggaagcccga tgcgccagag    660
ttgtttctga acatggcaa aggtagcgtt gccaatgatg ttacagatga gatggtcaga    720
ctaaactggc tgacggaatt tatgcctctt ccgaccatca agcatttat ccgtactcct     780
gatgatgcat ggttactcac cactgcgatc cccggcaaaa cagcattcca ggtattagaa    840
gaatatcctg attcaggtga aaatattgtt gatgcgctgg cagtgttcct gcgccggttg    900
cattcgattc ctgtttgtaa ttgtcctttt aacagcgatc gcgtatttcg tctcgctcag    960
gcgcaatcac gaatgaataa cggtttggtt gatgcgagtg attttgatga cgagcgtaat   1020
ggctggcctg ttgaacaagt ctggaaagaa atgcataagc ttttgccatt ctcaccggat   1080
tcagtcgtca ctcatggtga tttctcactt gataacctta ttttgacga ggggaaatta   1140
ataggttgta ttgatgttgg acgagtcgga atcgcagacc gataccagga tcttgccatc   1200
ctatggaact gcctcggtga gttttctcct tcattacaga acggctttt tcaaaaatat   1260
ggtattgata tcctgatat gaataaattg cagtttcatt tgatgctcga tgagttttc   1320
taatcagtac tgacaataaa aagattcttg ttttcaagaa cttgtcattt gtatagtttt   1380
tttatattgt agttgttcta ttttaatcaa atgttagcgt gatttatatt ttttttcgcc   1440
tcgacatcat ctgcccagat gcgaagttaa gtgcgcagaa agtaatatca tgcgtcaatc   1500
gtatgtgaat gctggtcgct atactgctgt cgattcgata ctaacgccgc catccagtgt   1560
cgaaaacgag ctctcgagaa cccttaatat aacttcgtat aatgtatgct atacgaagtt   1620
attaggtgat atcagatcca ctagtggcct atgcagggcc cagtatcatt atgacgttgt   1680
acctgacctt atga                                                    1694
```

<210> SEQ ID NO 5
<211> LENGTH: 1694
<212> TYPE: DNA
<213> ORGANISM: Artificial Sequence
<220> FEATURE:
<223> OTHER INFORMATION: integrative cassette used for deletion of gene
      ARE2

<400> SEQUENCE: 5

```
atggacaaga agaaggatct actggagaac gaacaatttc ccagctgaag cttcgtacgc    60
tgcaggtcga caacccttaa tataacttcg tataatgtat gctatacgaa gttattaggt   120
ctagagatct gtttagcttg cctcgtcccc gccgggtcac ccggccagcg acatggaggc   180
ccagaatacc ctccttgaca gtcttgacgt gcgcagctca ggggcatgat gtgactgtcg   240
cccgtacatt tagcccatac atccccatgt ataatcattt gcatccatac attttgatgg   300
ccgcacggcg cgaagcaaaa attacggctc ctcgctgcag acctgcgagc agggaaacgc   360
tcccctcaca gacgcgttga attgtcccca cgccgcgccc ctgtagagaa atataaaagg   420
ttaggatttg ccactgaggt tcttctttca tatacttcct tttaaaatct tgctaggata   480
cagttctcac atcacatccg aacataaaca accatgggta aggaaaagac tcacgtttcg   540
aggccgcgat taaattccaa catggatgct gatttatatg ggtataaatg gctcgcgat   600
aatgtcgggc aatcaggtgc gacaatctat cgattgtatg ggaagcccga tgcgccagag   660
ttgtttctga acatggcaa aggtagcgtt gccaatgatg ttacagatga gatggtcaga   720
ctaaactggc tgacggaatt tatgcctctt ccgaccatca agcattttat ccgtactcct   780
gatgatgcat ggttactcac cactgcgatc cccggcaaaa cagcattcca ggtattagaa   840
gaatatcctg attcaggtga aaatattgtt gatgcgctgg cagtgttcct gcgccggttg   900
cattcgattc ctgtttgtaa ttgtcctttt aacagcgatc gcgtatttcg tctcgctcag   960
gcgcaatcac gaatgaataa cggtttggtt gatgcgagtg attttgatga cgagcgtaat  1020
ggctggcctg ttgaacaagt ctggaaagaa atgcataagc ttttgccatt ctcaccggat  1080
tcagtcgtca ctcatggtga tttctcactt gataacctta ttttgacga ggggaaatta  1140
ataggttgta ttgatgttgg acgagtcgga atcgcagacc gataccagga tcttgccatc  1200
ctatggaact gcctcggtga gttttctcct tcattacaga acggctttt tcaaaaatat  1260
ggtattgata atcctgatat gaataaattg cagtttcatt tgatgctcga tgagtttttc  1320
taatcagtac tgacaataaa aagattcttg ttttcaagaa cttgtcattt gtatagtttt  1380
tttatattgt agttgttcta ttttaatcaa atgttagcgt gatttatatt tttttttcgcc  1440
tcgacatcat ctgcccagat gcgaagttaa gtgcgcagaa agtaatatca tgcgtcaatc  1500
gtatgtgaat gctggtcgct atactgctgt cgattcgata ctaacgccgc catccagtgt  1560
cgaaaacgag ctctcgagaa cccttaatat aacttcgtat aatgtatgct atacgaagtt  1620
attaggtgat atcagatcca ctagtggcct atgcgggacc aagtgtcatg tgtacgttgt  1680
acttgacatt ctaa                                                    1694
```

<210> SEQ ID NO 6
<211> LENGTH: 1095
<212> TYPE: DNA
<213> ORGANISM: Artificial Sequence
<220> FEATURE:
<223> OTHER INFORMATION: integrative cassette integrated into locus LEU2

<400> SEQUENCE: 6

```
atgtctgccc ctaagaagat cgtcgttttg ccaggtgacc acgttggtca agaaatcaca    60
gccgaagcca ttaaggttct taaagctatt tctgatgttc gttccaatgt caagttcgat   120
ttcgaaaatc atttaattgg tggtgctgct atcgatgcta caggtgttcc acttccagat   180
gaggcgctgg aagcctccaa gaaggctgat gccgttttgt taggtgctgt gggtggtcct   240
```

| | | | | |
|---|---|---|---|---|
| aaatggggta | ccggtagtgt | tagacctgaa | caaggtttac | taaaaatccg taaagaactt | 300 |
| caattgtacg | ccaacttaag | accatgtaac | tttgcatccg | actctcttttt agacttatct | 360 |
| ccaatcaagc | cacaatttgc | taaaggtact | gacttcgttg | ttgtcagaga attagtggga | 420 |
| ggtatttact | ttggtaagag | aaaggaagac | gatggtgatg | tgtcgcttg ggatagtgaa | 480 |
| caatacaccg | ttccagaagt | gcaaagaatc | acaagaatgg | ccgctttcat ggccctacaa | 540 |
| catgagccac | cattgcctat | ttggtccttg | gataaagcta | atgttttggc ctcttcaaga | 600 |
| ttatggagaa | aaactgtgga | ggaaaccatc | aagaacgaat | tccctacatt gaaggttcaa | 660 |
| catcaattga | ttgattctgc | cgccatgatc | ctagttaaga | acccaaccca cctaaatggt | 720 |
| attataatca | ccagcaacat | gtttggtgat | atcatctccg | atgaagcctc cgttatccca | 780 |
| ggttccttgg | gtttgttgcc | atctgcgtcc | ttggcctctt | tgccagacaa gaacaccgca | 840 |
| tttggtttgt | acgaaccatg | ccacggttct | gctccagatt | tgccaaagaa taaggtcaac | 900 |
| cctatcgcca | ctatcttgtc | tgctgcaatg | atgttgaaat | tgtcattgaa cttgcctgaa | 960 |
| gaaggtaagg | ccattgaaga | tgcagttaaa | aaggttttgg | atgcaggtat cagaactggt | 1020 |
| gatttaggtg | gttccaacag | taccaccgaa | gtcggtgatg | ctgtcgccga agaagttaag | 1080 |
| aaaatccttg | cttaa | | | | 1095 |

<210> SEQ ID NO 7
<211> LENGTH: 1295
<212> TYPE: DNA
<213> ORGANISM: Artificial Sequence
<220> FEATURE:
<223> OTHER INFORMATION: integrative cassette integrated into locus HO

<400> SEQUENCE: 7

| | | | | |
|---|---|---|---|---|
| atgctttctg | aaaacacgac | tattctgatg | gctaacggtg | aatgtggctg tggtttcagg | 60 |
| gtccataaag | cttttcaatt | catctttttt | ttttttgttc | tttttttga ttccggtttc | 120 |
| tttgaaattt | ttttgattcg | gtaatctccg | agcagaagga | agaacgaagg aaggagcaca | 180 |
| gacttagatt | ggtatatata | cgcatatgtg | gtgttgaaga | acatgaaat tgcccagtat | 240 |
| tcttaaccca | actgcacaga | acaaaaaacct | gcaggaaacg | aagataaatc atgtcgaaag | 300 |
| ctacatataa | ggaacgtgct | gctactcatc | ctagtcctgt | tgctgccaag ctatttaata | 360 |
| tcatgcacga | aaagcaaaca | aacttgtgtg | cttcattgga | tgttcgtacc accaaggaat | 420 |
| tactggagtt | agttgaagca | ttaggtccca | aaatttgttt | actaaaaaca catgtggata | 480 |
| tcttgactga | ttttttccatg | gagggcacag | ttaagccgct | aaaggcatta tccgccaagt | 540 |
| acaattttttt | actcttcgaa | gacagaaaat | ttgctgacat | tggtaataca gtcaaattgc | 600 |
| agtactctgc | gggtgtatac | agaatagcag | aatgggcaga | cattacgaat gcacacggtg | 660 |
| tggtgggccc | aggtattgtt | agcggtttga | agcaggcggc | ggaagaagta acaaaggaac | 720 |
| ctagaggcct | tttgatgtta | gcagaattgt | catgcaaggg | ctccctagct actggagaat | 780 |
| atactaaggg | tactgttgac | attgcgaaga | gcgacaaaga | ttttgttatc ggctttattg | 840 |
| ctcaaagaga | catgggtgga | agagatgaag | gttacgattg | gttgattatg acacccggtg | 900 |
| tgggtttaga | tgacaaggga | gacgcattgg | gtcaacagta | tagaaccgtg gatgatgtgg | 960 |
| tctctacagg | atctgacatt | attattgttg | gaagaggact | atttgcaaag ggaagggatg | 1020 |
| ctaaggtaga | gggtgaacgt | tacagaaaag | caggctggga | agcatatttg agaagatgcg | 1080 |
| gccagcaaaa | ctaaaaaact | gtattataag | taaatgcatg | tatactaaac tcacaaatta | 1140 |
| gagcttcaat | ttaattatat | cagttattac | ccgggaatct | cggtcgtaat gatttctata | 1200 |

```
atgacgaaaa aaaaaaaatt ggaaagaaaa agcttcatgg cctttataaa aaggataaga    1260
gttgtggtaa caacgcaggt gcgcgcatct gctaa                               1295
```

YEAST CELL FOR THE PRODUCTION OF TERPENES AND USES THEREOF

CROSS-REFERENCE TO RELATED APPLICATIONS

This application is a national phase of International Application No. PCT/EP2012/000665, filed Feb. 15, 2012, which claims priority from European Application No. EP11001629.2, filed Feb. 28, 2011.

The present invention relates to a yeast cell, wherein said cell comprises a functional gene coding for soluble hydroxymethylglutaryl-coenzyme-A (HMG-CoA) reductase; one or more gene(s) coding for steryl acyltransferase(s) in said cell are defective or deleted; and said cell is prototrophic for at least histidine, leucine or uracil. Moreover, the present invention relates to the use of said cell for the production of one or more terpene(s). Further, the present invention relates to methods of generating said cell and the production of one or more terperne(s) and a pharmaceutical or cosmetically composition, a lubricant or transformer oil comprising said terpene(s).

In today's pharmaceutical, cosmetically and chemical industry various terpenes are of increasing importance. Terpenes are used, e.g., as additives in pharmaceutical and cosmetically compositions, as adjuvants in vaccines, as skin moisteners, as mucolytic agents, as pheromones, as hormones, for pest control, as humectants, as fragrances, as lubricants, as antimicrobial agents, as anti-inflammatory agents, as food additives, as electric insulators, as transformer oil or transformer oil additives, and as useful raw chemicals in the chemical, pharmaceutical and cosmetic industry. Terpenes can further be used as a natural and sustainable source for chemical purposes.

Chemically, terpenes are derived from one or more isoprene unit(s), also designated as prenyl units. Isoprene bears the formula $CH_2=C(CH_3)-CH=CH_2$. Further, by conjugation of heteroatoms such as, e.g., oxygen or nitrogen, terpenes can be modified to terpenoids that are also known as isoprenoids.

In nature, most terpenes are found as secondary metabolites in plants, fungi and animals. Moreover, several bacteria produce terpenes. Terpenes can comprise different numbers of isoprene units. Hemiterpenes and derivatives thereof comprise a single isoprene unit and comprise, e.g., prenol and isovaleric acid. Monoterpenes and derivatives thereof comprise two isoprene units and comprise, e.g., geraniol, limonene and terpineol. Sesquiterpenes and derivatives thereof comprise three isoprene units and comprise, e.g., farnesenes, farnesol. Diterpenes and derivatives thereof are composed for four isoprene units and comprise, e.g., geranylgeranyl pyrophosphate, cafestol, kahweol, cembrene and taxadiene (precursor of taxol), retinol, retinal, and phytol. Sesterterpenes and derivatives thereof comprise five isoprene units and comprise, e.g., sesterterpenes are geranylfarnesol. Triterpenes comprise six isoprene units and comprise, e.g., squalene, lanosterol and cycloartenol. Tetraterpenes comprise, e.g., acyclic lycopene, the monocyclic gamma-carotene, and the bicyclic alpha- and beta-carotenes. Polyterpenes consist of long chains of numerous isoprene units and comprise, e.g., natural rubber and gutta-percha.

The vast majority of terpenes are derived from the enzymatically catalyzed mevalonate pathway. Herein, the formation of terpenes starts with acetyl-coenzyme A (CoA). Two acetyl-CoA molecules react enzymatically catalyzed to one acetoacetyl-CoA molecule. In the next step, acetoacetyl-CoA reacts with a further acetyl-CoA molecule to 3-hydroxy-3-methyl-glutaryl-CoA (hydroxymethylglutaryl-CoA; HMG-CoA). In the next step, HMG-CoA is reduced to mevalonate. This reaction is catalyzed by the enzyme HMG-CoA reductase and is typically the rate limiting step of terpene biosynthesis. Therefore, the HMG-CoA reductase is known as the key enzyme of the mevalonate pathway.

Mevalonate is typically phosphorylated twice and decarboxylated to isopentenyl-pyrophosphate (IPP). Through the sequential steps of isomerization, condensation and dehydrogenation, IPP is converted into geranyl-pyrophosphate, which is combined with a further IPP unit to farnesyl-pyrophosphate. Two molecules farnesyl-pyrophosphate reductively condense to squalene, which can be converted in cholesterol and any steroid hormone.

Alternatively, geranyl-pyrophosphate and farnesyl-pyrophosphate can further react to higher terpenes and, such as tetra- and polyterpenes.

A terpene of high importance is the triterpene is squalene. Worldwide, approximately 2000 tons of squalene are produced yearly. This leads to an annual turnover of approximately 125 million US dollar. Technically, squalene is preferably used as a nutritional additive, in cosmetics, and in the pharmaceutical industry. Further, squalene is also used as biodegradable lubricant and as transformer oil. Squalene can serve as an antioxidant and is further regularly used as adjuvant in vaccines.

Traditionally, squalene is obtained from biological sources, such as, e.g., fish oil, in particular shark liver oil. Then, squalene is purified from the complex composition of fish oil by laborious procedures. In the pharmaceutical field, the tracability of the product to be approved is very important for Health Authorities. But this tracability is difficult to assure when the product contains products coming from animal origin. For example, it is difficult to know exactly what the fish, such as a shark, has been eaten before being sacrificed. Thus, for a pharmaceutical product, it is important to use raw materials which are GMP complient, which means that their tracability can be obtained right from the origin. Further, several shark species are endangered species threatened with extinction. Terpenes other than squalene are likewise obtained from biological materials and have to be purified by laborious and often hazardous procedures.

Therefore, there is a need for alternative ways for the production or terpenes, such as squalene. The use of a genetically modified yeast strain producing higher yields of squalene has been demonstrated (EP 0 486 290). However, the described yeast strains further produce high amounts of steroids, such as, e.g., ergosterol. The production of steroids decreases the yield of squalene and other terpenes. Further, the presence of higher amounts of steroid impurities requires sophisticated methods to purify squalene and other terpenes from the raw material.

So far, the genetically modified organisms (GMOs) known in the art produce terpenes in a concentration that is too low for the efficient industrial production of terpenes and with too high impureness.

Moreover, genetically modified organisms are generally known to be genetically comparatively unstable and typically bear lower viability and/or growth kinetics than the corresponding wildtype cells, when cultivated. Therefore, during cultivation of a batch of said cells, the productivity of said batch typically decreases rapidly over time. This regularly hampers efficient usability of genetically modified organisms in variable industrial production methods.

Moreover, when generating a genetically modified organism by insertion of one or more foreign gene(s), one or more original gene(s) of the organism are replaced by said foreign gene. This may have the advantage that the cells become auxotrophic for certain organic nutrients, which may be used for selection purposes. Further, under certain cell culture conditions, auxotrophy is known to be able to have advantages for the reproducibility of the cells. Under certain conditions, prototrophic cells are even outcompeted by the corresponding auxotrophic cells. Exemplarily, it has been described that under ammonia-limited growth conditions, a histidine prototroph hoΔ::HIS3 yeast cell was competed out by the corresponding histidine auxotrophic cell HO his3 when cultivated for 30 generations (Pronk, 2002). Therefore, genetically modified organisms are often cultivated as auxotrophic strains. However, the use of auxotrophic cells evidently limits the freedom of choice of culture medium.

In the view of the above, there is still an unmet need for organisms that produce terpenes in a concentration and purity high enough for industrial usability that are genetically sufficiently stable.

Accordingly, the technical problem the present invention underlies is the provision of an organism with improved productivity of terpenes and improved genetic and phenotypic stability.

Surprisingly, it was found that a yeast cell comprising a functional gene coding for soluble hydroxymethylglutaryl-coenzyme-A (HMG-CoA) reductase, wherein one or more genes coding for the steryl acyltransferases have been deleted and that was prototrophic for histidine, leucine and uracil, bears a high productivity of terpenes and improved genetic and phenotypic stability in cell culture. Expectedly, the deletion of genes coding for steryl acyltransferases led to lower levels of steryl esters. However, unexpectedly, the deletion of genes coding for steryl acyltransferases did not lead to an accumulation of sterols, but rather to an accumulation of terpenes, such as squalene.

The generated cells form a stable cell line and are genetically stable when cultivated for more than 30 generation. Herein, it was surprisingly found that a cell that is prototrophic for histidine, leucine and uracil bears a higher genetic and phenotypic stability than a corresponding auxotrophic cell.

In a first aspect, the present invention relates to a yeast cell, wherein
  a.) said cell comprises a functional gene coding for soluble hydroxymethylglutaryl-coenzyme-A (HMG-CoA) reductase;
  b.) one or more gene(s) coding for steryl acyltransferase(s) in said cell are defective or deleted; and
  c.) said cell is prototrophic for at least histidine, leucine or uracil, preferably wherein said cell is at least prototrophic for histidine and leucine, histidine and uracil, or leucine and uracil, in particular wherein said cell is prototrophic for histidine, leucine and uracil.

As used herein, the term "yeast cell" may be understood in the broadest sense as any cell of a yeast organism. Preferably, the yeast cell may be a *Saccharomyces* cell, in particular a *Saccharomyces* cell selected from the group consisting of *Saccharomyces cerevisiae, Saccharomyces delbrückii, Saccharomyces italicus, Saccharomyces ellipsoideus, Saccharomyces fermentati, Saccharomyces kluyveri, Saccharomyces krusei, Saccharomyces lactis, Saccharomyces marxianus, Saccharomyces microellipsoides, Saccharomyces montanus, Saccharomyces norbensis, Saccharomyces oleaceus, Saccharomyces paradoxus, Saccharomyces pastorianus, Saccharomyces pretoriensis, Saccharomyces rosei, Saccharomyces rouxii, Saccharomyces uvarum, Saccharomycodes ludwigii*. Most preferably, the cell is a *Saccharomyces cerevisiae* cell. The *Saccharomyces cerevisiae* cell may be a cell of any strain, preferably a cell of the strain AH22 as used exemplarily in the examples.

Alternatively, the cell may be a non-*Saccharomyces* cell from *Kluyveromyces lactis, Kluyveromyces marxianus* var. *marxianus, Kluyveromyces thermotolerans, Candida utilis, Candida tropicalis, Candida albicans, Candida lipolytica* und *Candida versatilis*, of the genus *Pichia* like *Pichia stipidis, Piachia pastoris* und *Pichia sorbitophila, Cryptococcus, Debaromyces, Hansenula, Saccharomycecopsis, Saccharomycodes, Schizosaccharomyces, Wickerhamia, Debayomyces, Hanseniaspora, Kloeckera, Zygosaccharomyces, Ogataea, Kuraishia, Komagataella, Metschnikowia, Williopsis, Nakazawaea, Cryptococcus, Torulaspora, Bullera, Rhodotorula, Willopsis* or *Sporobolomyces*.

As used herein, the term "functional gene" means that the gene may be active in the yeast cell. Under suitable conditions, the gene may, therefore, be transcribed and translated in the yeast cell and the soluble hydroxymethylglutaryl-coenzyme-A (HMG-CoA) reductase polypeptide may be expressed. As used throughout the invention, the terms "polypeptide" and "protein" may be understood interchangeably.

The term "soluble hydroxymethylglutaryl-coenzyme-A (HMG-CoA) reductase" may be understood in the broadest sense as the soluble form of an enzyme catalyzing the reduction of hydroxymethylglutaryl-coenzyme-A (HMG-CoA) to mevalonate. As used herein, the terms "hydroxymethylglutaryl-coenzyme-A", "hydroxymethylglutaryl-CoA", "3-hydroxy-3-methyl-glutaryl-CoA", "3-hydroxy-3-methylglutaryl-CoA", "β-hydroxy-β-methyl-glutaryl-CoA", "β-hydroxy-β-methylglutaryl-CoA", "beta-hydroxy-beta-methyl-glutaryl-CoA", "beta-hydroxy-beta-methylglutaryl-CoA" and "HMG-CoA" may be understood interchangeably.

Preferably, in contrast to the wildtype form of HMG-CoA reductase, the soluble HMG-CoA reductase of the present invention may not be inhibited by one or more of the inhibitors of wildtype HMG-CoA, such as, e.g., mevalonate, glucagon, cholesterol, L-hydroxycholesterol, low density lipoproteins and bile acids.

Most preferably, the soluble HMG-CoA reductase is a truncated HMG-CoA reductase (tHMG1) as exemplarily used in the examples. This tHMG1 is further described by Basson et al. (Basson et al., 1988) and/or is coded by the DNA sequence of SEQ ID NO:1.

It may be understood that the soluble HMG-CoA reductase of the present invention may also be a product of one or more posttranslational modification(s). Posttranslational modifications are well-known in the art and may comprise but may not be limited to lipidation, phosphorylation, sulfation, glycosylation, truncation, cyclization of several amino acid moieties, cyclization of the polypeptide strand, oxidation, reduction, decarboxylation, acetylation, amidation, deamidation, disulfide bond formation, pyroglutamate formation, amino acid addition, cofactor addition (e.g., biotinylation, heme addition) and complexation of metal ions, non-metal ions, peptides or small molecules and addition of iron-sulfide clusters. Evidently, co-factors, such as, e.g., ATP, ADP, NAD+, NADH+H+, NADP+, NADPH+H+, metal ions, anions, lipids, etc. may be bound to the polypeptide, irrespective on the biological influence of these co-factors.

The term "soluble" as used herein refers to a form of the enzyme with decreased membrane binding properties. Preferably, more than 50% of the soluble HMG-CoA molecules of the present invention are not integrated into or attached to a membrane, more preferably more than 60% of the soluble HMG-CoA molecules of the present invention are not integrated into or attached to a membrane, even more preferably more than 70% of the soluble HMG-CoA molecules of the present invention are not integrated into or attached to a membrane, even more preferably more than 80% of the soluble HMG-CoA molecules of the present invention are not integrated into or attached to a membrane, even more preferably more than 90% of the soluble HMG-CoA molecules of the present invention are not integrated into or attached to a membrane, most preferably more than 95% of the soluble HMG-CoA molecules of the present invention are not integrated into or attached to a membrane. The soluble HMG-CoA reductase is preferably present in the cytosol of the yeast cell of the present invention.

The term "steryl acyltransferase" as used herein, refers to any enzyme catalyzing the formation of steryl acyl esters. The steryl acyltransferase may be a sterol O-acyltransferase. As used herein the terms "sterol O-acyltransferase", "sterol-ester synthase" and "acyl-CoA:sterol acyltransferase" may be understood interchangeably. In the context of the present invention, the sterol O-acyltransferase is preferably a yeast sterol O-acyltransferase (EC 2.3.1.26). More preferably, the sterol O-acyltransferase(s) is/are the gene product(s) of one or both of the sterol O-acyltransferases exemplarily used in the examples of the present invention, thus, the ARE1 gene and/or the ARE2 gene of yeast.

The ARE1 gene is also known as the SAT2 gene, ordered locus name YCR048W or ORF name YCR48W. The ARE2 gene is also known as the SAT1 gene, ordered locus name YNR019W or ORF name N3206.

In the context of the yeast cell of the present invention, the genes coding for steryl acyltransferase are deleted or defective. As used herein, the term "deleted" means that the gene or one or more part(s) of the gene have been removed. The gene is not transcribed and no gene product, thus no corresponding polypeptide, is produced. It may be understood that not necessarily the whole gene has to be removed from the genome. Preferably more than 50% of the gene, more preferably more than 60% of the gene, even more preferably more than 70% of the gene, even more preferably more than 80% of the gene, even more preferably more than 90% of the gene, even more preferably more than 95% of the gene, and most preferably 100% of the gene are deleted. The deletion may be a terminal deletion or an intercalary deletion. It may be caused by an experimenter or by nature. A gene may be deleted by any means known in the art. For instance, a gene may be deleted by crossing over or using cre-recombinase procedure (Guldener et al, 1996).

As used herein, the term "defective" means that the gene is either not transcribed or that the gene codes for a gene product, thus a polypeptide that is not functional. In the context of steryl acyl acyltransferases genes, the term "not functional" refers to a polypeptide having less than 50%, preferably less than 40%, more preferably less than 30%, even more preferably less than 20%, even more preferably less than 10%, even more preferably less than 5%, even more preferably less than 4%, even more preferably less than 3%, even more preferably less than 2%, and most preferably less than 1% of the acyl transferring efficiency compared to the corresponding wild-type polypeptide.

As exemplarily shown in the examples, the ARE1 and/or ARE2 gene(s) may preferably be deleted, in particular the ARE1 and ARE2 genes are deleted. A gene may be rendered defective by any means known in the art. For instance, the gene may be rendered defective by unspecific mutagenesis, caused by an experimenter of by nature (e.g., by radiation, chemical agents, or spontaneously) or by site-directed mutagenesis (e.g., by PCR). It can be caused by a frameshift or a point mutation (single nucleotide exchange).

Throughout the invention, the term "prototrophic" may be understood in the broadest sense as having the ability to synthesize a particular organic compound required for cell growth. In the context of the present invention, the yeast cell may be prototrophic for histidine, leucine and/or uracil. Therefore, the cell is able to synthesize histidine, leucine and/or uracil by itself and is therefore able to grow in histidine-, leucine- and/or uracil-free medium and on histidine-, leucine- and/or uracil-free cell culture plates. It may be understood that a yeast cell may also be prototrophic for other nutrient factors.

In a preferred embodiment, the yeast cell of the present invention is a cell of a stable cell line, preferably more stable than the corresponding cell which is at least auxotrophic for histidine, leucine or uracil, more preferably auxotrophic for histidine and leucine, histidine and uracil, or leucine and uracil, even more preferably auxotrophic for histidine, leucine and uracil.

As used herein, the term "stable cell line" may be understood as a cell population that maintains its phenotypic properties that are relevant in the context of the present invention. These relevant properties are mainly viability, growth and/or terpene productivity, most preferably viability, growth and terpene productivity.

It will be understood by a person skilled in the art that the stable cell line is preferably also genetically stable.

When cultivated for 30 generations, the terpene productivity preferably decreases not more than 50%, more preferably decreases not more than 30%, even more preferably not more than 20%, even more preferably not more than 10%, even more preferably not more than 8%, even more preferably not more than 6%, even more preferably not more than 4%, and most preferably not more than 2% compared to the yeast cells before cultivation for 30 generations.

Further, when cultivated for 30 generations, the cell reproduction rate preferably decreases not more than 50%, more preferably not more than 30%, even more preferably not more than 20%, even more preferably not more than 10%, even more preferably not more than 8%, even more preferably not more than 6%, even more preferably not more than 4%, and most preferably not more than 2% compared to the yeast cells before cultivation for 30 generations.

Moreover, the terpene productivity of the yeast cell of the present invention preferably does not decrease by more than 20% when cultivated for more than 10, more than 20, more than 30, more than 40, more than 50, more than 60, more than 70, more than 80, more than 90, more than 100, more than 150, or more than 200 generations.

Likewise, the cell reproduction rate of the yeast cell of the present invention preferably does not decrease by more than 20% when cultivated for more than 10, more than 20, more than 30, more than 40, more than 50, more than 60, more than 70, more than 80, more than 90, more than 100, more than 150, or more than 200 generations.

Throughout the invention, the term "auxotrophic" may be understood in the broadest sense as the inability of the yeast cell to synthesize a particular organic compound required for its growth. In the context of the present invention, a yeast cell may be auxotrophic for histidine, leucine and/or uracil. Therefore, the cell is unable to synthesize histidine, leucine and/or uracil by itself and is therefore not able to grow in histidine-, leucine- and/or uracil-free medium and on histidine-, leucine- and/or uracil-free cell culture plates. The auxotrophic yeast cell requires the respective supplementation of histidine, leucine and/or uracil in the culture medium. It may be understood that a yeast cell may also be auxotrophic for other nutrient factors of the group consisting of but not limited to vitamins, amino acids, sugars and lipid acids.

As used herein, the term "corresponding cell which is at least auxotrophic for histidine, leucine or uracil" refers to a cell of the same genetic origin as the cell of the present invention. The corresponding cell which is at least auxotrophic for histidine, leucine or uracil also comprises a functional gene coding for soluble HMG-CoA reductase. Further, one or more gene(s) coding for steryl acyltransferase(s) in said cell are deficient or deleted. The only genetic difference between the cell of the present invention and the corresponding cell which is at least auxotrophic for histidine, leucine and/or uracil is that the latter is at least auxotrophic for histidine, leucine and/or uracil. Preferably, the cell is a *Saccharomyces* cell, more preferably a *Saccharomyces cerevisiae* cell, even more preferably a *Saccharomyces cerevisiae* cell of the strain AH22, even more preferably a cell originated from the yeast strain AH22tH3 derived from the strain AH22, more preferably originated from the strain AH22tH3ura8, even more preferably originated from one of the strains AH22tH3ura8Δare1 or AH22tH3ura8Δare2. Most preferably, the corresponding cell which is at least auxotrophic for histidine, leucine or uracil is a yeast cell of the strain AH22tH3ura8Δare1Δare2 as exemplarily shown in the examples.

In a preferred embodiment, said cell is a genetically modified cell.

As used herein, the term "genetically modified cell" may be understood in the broadest sense as a cell which genome has been modified by any means known in the art also designated as genetically modified organism (GMO). The cell itself may be modified or may be a progeny of a cell genetically modified. Typically a GMO is generated by human experimenting, such as unspecific or specific mutagenesis by means of radiation (e.g, ultra violet (UV) radiation, X-ray radiation, radioactive/nuclear radiation (e.g., alpha-, beta- or gamma-radiation) or cosmic radiation) or one or more mutagenic agent(s) (e.g., alkylating agent (e.g., nitrogen mustards (e.g., cyclophosphamide, mechlorethamine or mustine (HN2), uramustine or uracil mustard, melphalan, chlorambucil, ifosfamide), nitrosoureas (e.g., carmustine, lomustine, streptozocin), alkyl sulfonates (e.g., busulfan), thiotepa and its analogues, platinum derivates (e.g., cisplatin, carboplatin, nedaplatin, oxaliplatin, satraplatin, triplatin tetranitrate), procarbazine, altretamine, aflatoxine and aflatoxine and metabolic products and derivatives thereof, nitrite, aniline and metabolic products and derivatives thereof, benzene and metabolic products and derivatives thereof, polycyclic aromatics and metabolic products and derivatives thereof) to a nucleobase), nitrosamines, arsenic, asbestos, beryllium and its compounds, ethylene oxide, hexavalent chromium(VI) compounds, radon, vinyl chloride, smoking, etc.). However, a mutation may also spontaneously occur.

In a preferred embodiment, said cell is a *Saccharomyces* cell, more preferably wherein said cell is a *Saccharomyces cerevisiae* cell, in particular wherein, said cell is derived from a *Saccharomyces cerevisiae* cell of the strain AH22.

Yeast cells of the strain AH22 are commercially obtainable from the American Type Culture Collection (ATCC) under ATCC number 38626. Originally, the AH22 strain having a leu2⁻ double mutation and the genotype a' leu2-3 leu2-112 his4-519 can1 was derived from wildtype strain S288c (Hinnen et al., 1978). The S288c strain (Mortimer et al., 1985) is also commercially available under ATCC number 26108. Preferably, the yeast cell of the present invention is a *Saccharomyces cerevisiae* cell originated from the strain AH22tH3 that has been derived from a cell of the strain AH22, more preferably originated from the strain AH22tH3ura8, even more preferably originated from one of the strains AH22tH3ura8Δare1, AH22tH3ura8Δare2 or AH22tH3ura8Δare1Δare2, even more preferably originated from the strain AH22tH3ura8Δare1Δare2, even more preferably originated from one of the strains AH22tH3ura8Δare1Δare2H, AH22tH3ura8Δare1Δare2U or AH22tH3ura8Δare1Δare2L. Most preferably, the yeast cell of the present invention is a yeast cell of the strain AH22tH3ura8Δare1Δare2HUL as exemplarily shown in the examples.

In a further preferred embodiment, the soluble HMG-CoA reductase is characterized in that
  a.) it is a truncated soluble HMG-CoA reductase protein lacking the membrane-binding region;
  b.) it is encoded on a vector under the transcriptional control of a promoter that is active in said cell; and/or
  c.) it is expressed under the control of a constitutive promoter, in particular under the control of a strong constitutive promoter.

In context of the present invention, the term "truncated soluble HMG-CoA reductase protein" refers to a HMG-CoA reductase protein of a shorter length than the wildtype HMG-CoA reductase protein with respect to the length of the constitutive amino acid strand. Preferably, the HMG-CoA reductase protein lacks the membrane-binding region of the wildtype protein.

As used herein, the term "membrane-binding region" refers to a region in the polypeptide strand relevant for the integration into the membrane or the attachment to the membrane. It is known in the art that the amino-terminal 525 amino acids of the HMG-CoA reductase are mostly integrated into the membrane (Basson et al., 1988).

Therefore, in the context of the present invention, preferably the amino-terminal amino acids up to an amino acid position in between a range from approximately 450 to 500, from approximately 500 to 510, from approximately 510 to 520, from approximately 520 to 530, from approximately 530 to 540, from approximately 540 to 550, from approximately 550 to 560, from approximately 560 to 570 or from approximately 570 to 600 amino acids may be truncated. Exemplary, amino acids up to amino acid 552, thus amino acids 1 to 552, may be truncated (Polakowski et al., 1998). Most preferably, the truncated soluble HMG-CoA reductase is tHMG1 as described by Basson et al. (Basson et al., 1988). tHMG1 is coded by the DNA sequence of SEQ ID NO:1.

In contrast to the wildtype form of HMG-CoA reductase, the truncated soluble HMG-CoA reductase of the present invention may not be inhibited by one or more of the inhibitors of wildtype HMG-CoA, such as, e.g., mevalonate, glucagon, cholesterol, L-hydroxycholesterol, low density lipoproteins and bile acids.

Most preferably, the soluble HMG-CoA reductase is the truncated HMG-CoA reductase tHMG1 as exemplarily used in the examples. This tHMG1 is further described by Basson et al. (Basson et al., 1988) and/or is coded by the DNA sequence of SEQ ID NO:1.

As indicated above, it may be understood that the soluble HMG-CoA reductase of the present invention may also be a product of one or more posttranslational modification(s). Posttranslational modifications are well-known in the art and may comprise but may not be limited to lipidation, phosphorylation, sulfation, glycosylation, truncation, cyclization of several amino acid moieties, cyclization of the polypeptide strand, oxidation, reduction, decarboxylation, acetylation, amidation, deamidation, disulfide bond formation, pyroglutamate formation, amino acid addition, cofactor addition (e.g., biotinylation, heme addition) and complexation of metal ions, non-metal ions, peptides or small molecules and addition of iron-sulfide clusters. Evidently, co-factors, such as, e.g., ATP, ADP, NAD+, NADH+H+, NADP+, NADPH+H+, metal ions, anions, lipids, etc. may be bound to the polypeptide, irrespective on the biological influence of these co-factors.

As used in the context of the present invention, the term "vector" may refer to any composition transferring genetic information into the yeast cell. The genetic information may be encoded as deoxyribonucleic acid (DNA) (double stranded DNA (dsDNA), single stranded DNA (ssDNA)), ribonucleic acid (RNA), (single-stranded RNA (ssRNA), double-stranded RNA (dsRNA)), or as a DNA analog such as, e.g., peptide nucleic acid (PNA), morpholino, glycol nucleic acid (GNA), threose nucleic acid (TNA) or methylated DNA. Preferably, the genetic information is encoded as DNA. The vector may be any vector known in the art such as, e.g., a linear vector, a circular vector, a viral vector or a bacterial vector. Preferably, the vector comprises linear DNA or circular DNA, more preferably circular DNA, in particular a plasmid. The vector may be inserted into the cell by any means known in the art, and may be used in combination with or without transfecting agent(s) (e.g., lithium acetate, polyethylene imine (PEI), fugene, LT-1, JetPEI, transfectamine, lipofectamine, UptiFectin, PromoFectin, GenePORTER, Hilymax, carbon nanofibres, carbon nanotubes cell-penetrating peptides (CPPs), protein transduction domains (PTDs), liposomes, DEAE-dextran, dendrimers), with or without electroporation, or with or without a gene gun, with or without optical transfection with or without gene electrotransfer, with or without impalefection, with or without magnetofection, and/or with or without magnet assisted transfection. Preferably, the vector is a circular DNA vector, more preferably, the vector is a plasmid. The plasmid may be any plasmid known in the art such as, e.g., a YEpH2 or a pUC19 plasmid. The vector may also be a linear expression cassette that may or may not be integrated in the genome of the target cell. However, it may be understood that every other vector may also be used.

The term "under the transcriptional control" means that the promoter regulates the transcription rate of the gene. The transcription rate is the rate of messenger RNA (mRNA) complementary to a segment of the antisense strand of the vector DNA generated per time interval.

As used herein, the term "promoter" may be understood in the broadest sense as a region of DNA that facilitates the transcription of the gene coding for soluble HMG-CoA reductase. The promoter may be located near the gene, and may be located on the same strand and upstream. Upstream means that it is located towards the 5' region of the sense strand coding for the soluble HMG-CoA reductase. The promoter may be a homologous promoter or a heterologous promoter. Most preferably, the promoters as exemplarily shown in the examples are used.

The term "expressed" may be understood in the broadest sense as the conversion of genetic information into a polypeptide strand.

The term "constitutive promoter" may be understood as an extensively unregulated promoter that allows continual transcription of its associated gene. The term "strong constitutive promoter" refers to a promoter that bears a high transcriptional rate.

Further, in a preferred embodiment, the one or more gene(s) coding for steryl acyltransferase(s) is/are ARE1 and/or ARE2, preferably both genes, ARE1 and ARE2, are defective or deleted.

Additionally or alternatively, other genes that have an influence on the formation of steryl acyl esters may be defective or deleted.

In a preferred embodiment, the terpene productivity, preferably the triterpene productivity, in particular the squalene productivity of said cell is at least equivalent, preferably increased in comparison with the corresponding wildtype cell and/or the corresponding cell which is at least auxotrophic for histidine, leucine or uracil, preferably auxotrophic for histidine and leucine, histidine and uracil, or leucine and uracil, more preferably auxotrophic for histidine, leucine and uracil.

The term "terpene" may be understood in the broadest sense as any molecule structurally derived from isoprene. Preferably, the terpene of the present invention is a terpene comprising at least two isoprene units, more preferably the terpene comprises at least three isoprene units, even more preferably the terpene comprises at least four isoprene units, even more preferably the terpene comprises at least five isoprene units, even more preferably the terpene comprises six isoprene units, in particular, the terpene is a triterpene.

Preferably, the terpene is a terpene derived from the mevalonate pathway. These terpenes comprise, but are not limited to squalene, carotene (e.g., α-carotene, β-carotene, γ-carotene, δ-carotene, ε-carotene, ζ-carotene), carotenoid, retinoate, retinoic acid complex, retinyl ester, retinal (all-trans retinal, 11-cis-retinal), retinol (vitamin A, all-trans retinol, 11-cis-retinol), farnesene, farnesol, geranene, geranol, isopentene, quinonol (e.g., phylloquinonol, plastoquinonol, ubiquinonol, menaquinonol), phytene, phytenol, geranylgeranene, geranylgeranenol, xanthophyll (e.g., violaxanthin, zeaxanthin), isopentol, limonene, limonol, pinene, pinol, juvenile hormone III, undecaprene, undecaprenol, undecaprenyl sugar, kaurene, kaurenol, phytoalexin, capsidiol, guaiaazulene, giberillin, rubber, tocopmerol, chlorophyll, quinone (e.g., phylloquinone, plastoquinone, ubiquinone, menaquinone), dolichol, dolechyl sugar, prephytoene, phytoene, phytoenol, phytofluene, phytofluenol, neurosporene, lycopene, lycopenol, lycoprene, and lycoprenol, cafestol, kahweol, cembrene, cambrenol, taxadiene, paclitaxel, taxol, sesterterpene, cycloartenol, natural rubber, or gutta-percha.

The terpene may or may not comprise one or more heteroatom(s), preferably oxygen and/or nitrogen. It will be understood that a terpene comprising one or more hydroxyl group(s) may also be esterified with, e.g., phosphate, pyrophosphate, one or more fatty acid(s), one or more amino acid(s), one or more polypeptide(s), and/or one or more short peptide(s). Further, a terpene comprising one or more amino group(s) may be amidated with, e.g., phosphate, pyrophosphate, one or more fatty acid(s), one or more amino acid(s), one or more polypeptide(s), and/or one or more short peptide(s). Moreover, a terpene comprising one or more carboxylic group(s) may be amidated with, e.g., one or more amino acid(s), one or more polypeptide(s), and/or one or more short peptide(s) and/or may be esterified with e.g., one or more coenzyme(s) (e.g., coenzyme A (CoA)), one or more sugar(s), one or more amino acid(s), one or more polypeptide(s), and/or one or more short peptide(s). Preferably, the terpene is unconjugated, or esterified with phosphate, pyrophosphate and/or CoA. More preferably, the terpene is unconjugated. Most preferably, the terpene is squalene as exemplarily shown in the examples.

The term "terpene productivity" may be understood as the productivity of any terpene by the yeast cell. Preferably terpene productivity refers to the productivity of a terpene of the mevalonate pathway, more preferably to squalene productivity.

As used throughout the invention, the term "productivity" may be understood in the broadest sense as the ability of the cell of the present invention to produce a particular molecule. The productivity may be quantified as the amount of said molecule that a cell produces in a certain time interval. Therefore, productivity may be understood as production of a particular molecule over time. Preferably, the productivity of a batch of cells may be quantified as the mass of the particular molecule per volume of culture broth, as mass of said molecule per cell or as percent per weight (% (w/w)) per cell dry mass. If the productivity of two strains, such as, e.g., the strain of the present invention versus the corresponding wildtype strain is compared with another, the relative productivity may be quantified as increase or decrease of production of a terpene in percent per weight.

As used in the context of the present invention, the term "wildtype cell" refers to a yeast cell of the same species that is not genetically modified. The wildtype cell may preferably be of the same strand from which the yeast cell of the present invention is derived from. More preferably, the wildtype cell does not comprise a functional gene coding for soluble HMG-CoA reductase and/or said wildtype cell does comprise a functional ARE1 gene and/or a functional ARE2 gene. The wildtype cell may be a naturally occurring cell and/or may be obtainable from a cell bank such as e.g., the American Type Culture Collection (ATCC).

The term "corresponding wildtype cell" refers to a wildtype cell that originates of the same genetic origin as the cell of the present invention, but wherein one or more genetic mutations do not occur. The corresponding wildtype cell is of the same species and originates of the same strain as the yeast cell of the present invention. Further, the corresponding wildtype cell may preferably have no deletion of deficiency in the ARE 1 and/or ARE2 gene, in particular in the ARE1 and the ARE2 gene. Preferably, the wildtype cell is yeast cell, more preferably a *Saccharomyces* cell, even more preferably a *Saccharomyces cerevisiae* cell, even more preferably a *Saccharomyces cerevisiae* cell of a commercially available strain, even more preferably a *Saccharomyces cerevisiae* cell of strain AH22 or S288c. Most preferably, the wildtype cell is a *Saccharomyces cerevisiae* cell of strain AH22.

The term "equivalent" refers to a terpene productivity that is identical with the corresponding wildtype cell and/or the corresponding auxotrophic cell as defined above within an error range of +/−20%, more preferably within an error range of +/−10%, even more preferably within an error range of less than +/−10%.

In a preferred embodiment, said cell produces reduced amounts of steryl acyl esters, preferably wherein said cell is deficient for the production of steryl acyl esters.

As used herein, the term "reduced amount" refers to the production of a lower amount of a steryl ester. The production of a reduced amount may refer to a steryl acyl esters productivity of less than 100%, less than 50%, less than 40%, less than 30%, less than 20%, less than 10%, less than 8%, less than 6%, less than 5%, less than 4%, less than 3%, less than 2%, or even less than 1% of the amount produced by the corresponding wildtype cell. Exemplarily, the corresponding wildtype cell may be a yeast cell of the AH22 strain or a yeast cell of the S288c strain, in particular a cell of the AH22 strain.

The term "deficient for the production of steryl acyl esters" may be understood as the extensive absence of the formation of steryl esters. It will be understood that in a biological system there will be always a basal level of unspecific activity. Therefore, as used herein, the term "extensive absence" may refer to a concentration of less than 5%, preferably less than 1%, more preferably less than 0.5%, even more preferably less that 0.1% of the concentration found in a corresponding wildtype cell.

A second aspect of the present invention relates to a method of generating a cell of the present invention, said method comprising:
  a.) inserting a gene coding for soluble HMG-CoA reductase into a yeast cell;
  b.) selecting cells comprising a gene coding for said soluble HMG-CoA reductase;
  c.) deleting or mutating one or more gene(s) coding for steryl acyltransferase(s) of said cell;
  d.) converting said cell into a cell that is at least prototrophic for histidine, leucine and/or uracil, preferably histidine and leucine, histidine and uracil, or leucine and uracil, even more preferably for histidine, leucine and uracil, by means of
    (i) inserting gene cassette(s) coding for one or more enzyme(s) for the production of histidine, leucine and/or uracil, and/or
    (ii) revertant mutagenesis of one or more defective gene(s) coding for enzymes for the production of histidine, leucine and/or uracil, in particular by revertant mutagenesis of a defective gene coding for an enzyme for the production of histidine and by inserting gene cassettes coding for enzymes for the production of leucine and uracil;
  e.) selecting cells that are prototrophic for histidine, leucine and/or uracil, preferably cells that are at least prototrophic for histidine and leucine, histidine and uracil, or leucine and uracil, in particular cells that are prototrophic for histidine, leucine and uracil; and optionally;
  f.) cultivating cells of step e.); and optionally
  g.) isolating and stabilizing the cells of step e.) or f.).

The yeast cell and its functional features are detailed above. It will be understood that the features defined therein also apply to a cell generated by a method of the present invention.

As used herein the term "generating a cell" may be understood in the broadest sense as the provision of the cell of the present invention. It will be understood that the parent cell may be any yeast cell. Preferably, the cell is a cell of a wildtype strain. Exemplarily, as detailed above, the wildtype strain may be the AH22 strain or the S288c strain, preferably the AH22 strain. Most preferably, the cell is generated as exemplarily shown in the examples.

The term "inserting a gene" refers to any means of incorporating a gene into the yeast cell. The gene may be encoded on any carrier of genetic information such as, e.g, DNA (double-stranded DNA (dsDNA), single stranded DNA (ssDNA)), RNA (single-stranded RNA (ssRNA), double-stranded RNA (dsRNA)), a DNA analog such as, e.g., peptide nucleic acid (PNA), morpholino, glycol nucleic acid (GNA), threose nucleic acid (TNA) or methylated DNA, or a hybrid thereof. Preferably, the gene is encoded on DNA, more preferably double stranded DNA, in particular a circular double stranded DNA strand, in particular a plasmid. The plasmid may be any plasmid known in the art. Exemplarily, the plasmid may be the YEpH2 or a pUC plasmid. Most preferably, the one or more gene(s) may be inserted as exemplarily shown in the examples.

The genetic information may be inserted into the cell as a vector. As detailed above, the vector may be any vector known in the art such as, e.g., a linear vector, a circular vector, a viral vector or a bacterial vector. Preferably, the vector comprises linear DNA or circular DNA, more preferably circular DNA, in particular a plasmid The vector may be inserted into the cell by any means known in the art, and may be used in combination with or without transfecting agent(s) (e.g., polyethylene imine (PEI), Fugene, LT-1, JetPEI, transfectamine, lipofectamine, UptiFectin, PromoFectin, GenePORTER, Hilymax, carbon nanofibres, carbon nanotubes cell-penetrating peptides (CPPs), protein transduction domains (PTDs), liposomes, DEAE-dextran, dendrimers), with or without electroporation, or with or without a gene gun, with or without optical transfection with or without gene electrotransfer, with or without impalefection, with or without magnetofection, and/or with or without magnet assisted transfection. Preferably, the vector is a circular DNA vector, more preferably, the vector is a plasmid. The plasmid may be any plasmid known in the art such as, e.g., a YEpH2 or a pUC19 plasmid. However, it may be understood that every other vector may also be used.

The inserted gene may be active or passive in the cell. Preferably, the inserted gene is actively transcribed and expressed in the cell. The gene may be actively transcribed and expressed as extranuclear plasmid, as intranuclear plasmid, as extranuclear linear vector, as intranuclear linear vector, or may be inserted into the genome of the yeast cell. As used herein, the term "genome" refers to the entity of genetic information in the yeast cell. Preferably, the gene coding for soluble HMG-CoA reductase is inserted into the genome of said yeast cell. Optionally, the HMG-CoA reductase may replace another gene, such as e.g, a gene for uracil prototrophy such as, e.g., the ura3 gene. The resulting cell is then auxotrophic for uracil.

Preferably, said gene coding for soluble HMG-CoA reductase is expressed in the yeast cell, thus, soluble HMG-CoA reductase is produced by said cell.

As used throughout the invention, the term "selecting cells" refers to the enrichment of the desired fraction of the cell population. Most preferably, the cells are selected as exemplarily shown in the examples.

In the context of cells comprising a gene coding for said soluble HMG-CoA reductase, the cells comprising said gene are enriched in the population. Selection of the cells may be performed in a suspension culture or on a culture plate of solid material such as, e.g, an agar plate. The cells may be selected by dilution of the cells and streaking them out to generate colonies originating from a single cell only. Preferably, these colonies are subsequently tested for the presence of a gene coding for said soluble HMG-CoA reductase. Alternatively, the cells may be functionally tested by determining the productivity of terpenes. Alternatively or additionally, the cells may also be selected by subjecting the cells to a selection pressure. This selection pressure may be an antibiotic to which only the desired cell population is resistant to or may be a growth condition preferred by the desired population. In the context of selecting cells comprising a gene coding for said soluble HMG-CoA reductase, the cells may be grown on or in a medium preferred by the cells comprising said gene. Exemplarily, if the incorporation of the gene coding for said soluble HMG-CoA reductase into the yeast cell's genome replaces a gene for uracil prototrophy, the cell culture medium may contain 5-FOA (5-fluoroorotic acid) (Boeke et al., 1987) that promotes the selection of uracil-auxotrophic yeasts.

As used herein, the term "deleting a gene" may be understood as the removal of a gene or one or more part(s) of said gene. Then, the gene is not transcribed and no gene product, thus no corresponding polypeptide, is produced. It may be understood that not necessarily the whole gene has to be removed from the genome. Preferably more than 50% of the gene, more preferably more than 60% of the gene, even more preferably more than 70% of the gene, even more preferably more than 80% of the gene, even more preferably more than 90% of the gene, even more preferably more than 95% of the gene, and most preferably 100% of the gene are deleted. The deletion may be a terminal deletion or an intercalary deletion. It may be caused by an experimenter of by nature. A gene may be deleted by any means known in the art. For instance, a gene may be deleted by crossing over or by using cre-recombinase procedure (Guldener et al, 1996). Most preferably, the one or more gene(s) may be deleted as exemplarily shown in the examples.

As used herein, the term "mutating a gene" may be understood in the broadest sense as an alteration of the nucleic acid sequence of said gene. The resulting mutation may be a single nucleotide exchange (point mutation) or may be a frameshift mutation. Preferably, the gene is mutated in a way that it does not result in a gene product, i.e., a polypeptide, or in a polypeptide with decreased activity compared to the wildtype polypeptide. A mutation may be caused by any means known in the art (e.g., by radiation or chemical agents), or by site-directed mutagenesis (e.g., by PCR). The mutation may also occur spontaneously due to the naturally occurring mutation rate. The mutation may cause a frameshift or a point (single nucleotide) mutation. For instance, the mutation may be obtained by unspecific mutagenesis, caused by an experimenter or by nature. Most preferably, the one or more gene(s) may be mutated as exemplarily shown in the examples.

A mutation may be caused by, e.g., radiation (e.g, ultra violet (UV) radiation, X-ray radiation, radioactive/nuclear radiation (e.g., alpha-, beta- or gamma-radiation) or cosmic radiation) or one or more mutagenic agent(s) (e.g., alkylating agent (e.g., nitrogen mustards (e.g., cyclophosphamide, mechlorethamine or mustine (HN2), uramustine or uracil mustard, melphalan, chlorambucil, ifosfamide), nitrosoureas (e.g., carmustine, lomustine, streptozocin), alkyl sulfonates (e.g., busulfan), thiotepa and its analogues, platinum derivates (e.g., cisplatin, carboplatin, nedaplatin, oxaliplatin, satraplatin, triplatin tetranitrate), procarbazine, altretamine, aflatoxine and aflatoxine and metabolic products and derivatives thereof, nitrite, aniline and metabolic products and derivatives thereof, benzene and metabolic products and derivatives thereof, polycyclic aromatics and metabolic products and derivatives thereof) to a nucleobase), nitrosamines, arsenic, asbestos, beryllium and its compounds, ethylene oxide, hexavalent chromium(VI) compounds, radon, vinyl chloride, smoking, etc.). A mutation may also spontaneously occur.

Preferably, the steryl acyltransferase(s) is are ARE1 and/or ARE2. Preferably, the ARE1 and/or ARE2 gene(s) is/are deleted, more preferably the ARE1 and ARE2 genes are deleted.

The term "converting" may be understood in the broadest sense as altering of the genetic properties of a cell. One or more gene cassette(s) coding for one or more enzyme(s) for the production of histidine, leucine and/or uracil may be inserted into the cells or by revertant mutagenesis of one or more defective gene(s) coding for enzymes for the production of histidine, leucine and/or uracil. Most preferably, the cells are converted as exemplarily shown in the examples.

As used herein, the term "gene cassette" may be understood in the broadest sense as a modular DNA sequence encoding one or more gene(s) for a single biochemical function. It may refer to a manipulable fragment of DNA carrying one or more gene(s) of interest, being capable of expressing, one or more of said gene(s) and may further comprise one or more set(s) of restriction sites. Preferably, the one or more gene(s) are located in between two or more restriction sites. Optionally, the gene cassette may be transferred from one DNA sequence (usually on a vector) to the genome and replace a DNA sequence of the genome of the cell of the present invention. Most preferably, the gene cassette(s) may be deleted as exemplarily shown in the examples.

In the context of the present invention, the term "revertant mutagenesis" refers to a mutation that restores the former genotype or the original phenotype of the corresponding wildtype cell with respect to particular phenotypic feature(s). Then, preferably, a defective gene is repaired. Exemplarily a revertant mutation of a defective gene coding for an enzyme for the production of histidine in a histidine-auxotrophic cell may lead to a histidine-prototrophic cell. Most preferably, the revertant mutagenesis may be performed as exemplarily shown in the examples.

The defective gene coding for an enzyme for the production of histidine may be repaired by inserting a gene cassette or by revertant mutagenesis. Preferably, the gene is repaired by revertant mutagenesis, more preferably by revertant mutagenesis of the HIS4 gene.

The defective gene coding for an enzyme for the production of leucine may be repaired by inserting a gene cassette or by revertant mutagenesis. Preferably, the gene is repaired by inserting a gene cassette comprising an intact form of said gene, more preferably by inserting a gene cassette coding for the LEU2 gene.

The defective gene coding for an enzyme for the production of uracil may be repaired by inserting a gene cassette or by revertant mutagenesis. Preferably, the gene is repaired by inserting a gene cassette comprising an intact form of said gene, more preferably by inserting a gene cassette coding for the URA3 gene.

In the context of cells prototrophic for histidine, leucine and/or uracil, the prototrophic cells are enriched in the population. Selection of the cells may be performed in a suspension culture or on a culture plate of solid material such as, e.g, an agar plate. The cells may be selected by dilution of the cells and streaking them out to generate colonies originating from a single cell only. These colonies may subsequently be tested for the presence of the respective genes or by their phenotypic properties. Alternatively or additionally, the cells may also be selected by subjecting the cells to a selection pressure. This selection pressure may be a medium lacking the respective compound or a medium comprising an antibiotic to which only the desired cell population is resistant to or may be a growth condition preferred by the desired population. Preferably, the medium lacks histidine, leucine and/or uracil, more preferably said medium lacks histidine and leucine, histidine and uracil, or leucine and uracil, in particular said medium lacks histidine, leucine and uracil. As used herein, the term "lacks" means that the concentration of said compound is not present or only present in traces.

The term "cultivating cells" may be understood in the broadest sense as keeping the cells viable. The cells may be cultivated at conditions suitable for yeast cells. Exemplarily, yeast cells may be cultivated in suspension culture or on plates such as, e.g., agar plates. The suspension medium or agar may contain nutrients suitable for the yeast cells such as, e.g., one or more amino acid(s), one or more peptide(s), one or more lipid(s), one or more vitamin(s), trace elements, and/or salts, one or more growth factor(s) and one or more buffer(s). The cells may be cultivated at aerobic or anaerobic conditions. The temperature may be in a suitable range for the cells known by those skilled in the art. Exemplarily for yeasts, the temperature may typically be in the range of between 18° C. and 40° C., preferably between 20° C. and 37° C., more preferably in the range of between 20° C. and 30° C., even more preferably at 25° C. to 30° C., most preferably at 30° C. The pH value of the medium may be in a range suitable for the yeast cell. For most yeast cells suitable pH may be in a neutral or slightly basic pH. Most preferably, the cells are cultivated as exemplarily shown in the examples.

Preferably, the cultivation of cells leads to the reproduction of the cells. Reproduction may occur form cell division of the yeast cell(s), budding of the yeast cell(s), formation of spores, formation of one or more gamete(s) and/or sexual reproduction. More preferably, the reproduction of the yeast cell(s) is cell division or budding.

Cultivation of the cells may include cultivation in laboratory scale, i.e., cultivation of several culture plates or suspension cultures of several milliliters up to few liters culture broth. Cultivation of the cells may further include cultivation in a semi-technical scale, i.e., cultivation of suspension cultures of several liters culture broth and cultivation in an industrial scale, i.e., cultivation of suspension cultures of several liters or even several square meters culture broth. As used herein, the term "culture broth" comprises the cells and the medium. A suspension culture may optionally be stirred or shaken. A suspension culture may optionally be aerated, ventilated and/or degassed. The cells may be cultivated at a suitable pressure, the pressure may be atmospheric pressure, excess pressure or underpressure. Typically the cells may be cultivated at atmospheric pressure or slight excess pressure.

For terpene production, the cells may be cultivated for any time, preferably for at least 30 min, at least 2 h, at least 10 h, at least 24 h, at least 48 h, at least 72 h, or even for up to a week, up to a month, or up to several months. The cells may be cultivated for several generations. The cells may be cultivated for more than 1 generation, for more than 5 generations, for more than 10 generations, for more than 15 generations, for more than 20 generations, for more than 25 generations, for more than 30 generations, for more than 35 generations, for more than 50 generations, for more than 100 generation, or even longer.

As used in the context of the present invention, the term "isolating" in the context of cells refers, in the broadest sense, to the concentration of the cells of the present invention. The cells may be harvested. The cells may be isolated by any means known in the art such as, e.g., centrifugation, filtration, crossflow filtration, chromatography (e.g., affinity, size exclusion, ion-exchange chromatography), or abrasion or swabbing off a solid surface or culture plate. Alternatively, the cells may decent over time or may float due to gassing of the container comprising said cells. Alternatively, the cells are not isolated, but the cells and the medium are treated further together.

The isolated cells may further be washed with a suitable buffer or culture medium. Preferably, the cells may be washed by centrifugation, filtration, crossflow filtration, or chromatography (e.g., affinity, size exclusion, ion-exchange chromatography). The isolated cells may be analyzed by any means known in the art. The isolated cells may be disrupted, streaked out on culture plates, inoculated in a suspension culture or may be stabilized. Most preferably, the cells are isolated as exemplarily shown in the examples.

As used in the context of the present invention, the term "stabilizing" in the context of cells refers, to any means of conservation of cells. Preferably, the cells are stabilized in a way that they can be stored for a comparably long time and can be used to form a viable cell culture later.

The cells may be stabilized by freezing, freeze-drying or drying. Preferably, the cells are frozen. The cells may be frozen at −20° C., −80° C., on dry ice or in liquid nitrogen.

Preferably, the cells may be frozen in a medium suitable to freeze yeast cells. This medium may contain glycerol. Preferably, the cells may be stabilized in aqueous buffers or water supplemented with more than 2% (v/v), more than 5% (v/v), more than 10% (v/v), more than 20% (v/v), more than 30% (v/v), more than 40% (v/v), or more than 50% (v/v) glycerol. Exemplarily, yeast cells may be frozen in medium comprising 50% (v/v) glycerol in water. As used throughout the invention, the abbreviation v/v refers to volume per volume. A batch of cells stabilized in a glycerol solution may be designated as glycerol stock. Alternatively, the yeast cells may be dried or freeze-dried, preferably by the addition of an emulsifier such as, e.g., a citric aci.e.er. Dried or freeze-dried cells may be stored at dry conditions at any temperature such as, e.g., at room temperature, ambient temperature, at −4° C., −20° C., −80° C., on dry ice or in liquid nitrogen. Most preferably, the cells are stabilized as exemplarily shown in the examples.

The stabilized cells may be stable for at least more than 1 day, preferably more than 5 days, more preferably more than 1 week, even more preferably more than 1 month, and even more preferably more than 1 year. As indicated above, "stable" means that the cell can be used to form a viable cell culture after the storage time.

Alternatively, the cells are not isolated, but the cells and the medium are treated further together.

In a preferred embodiment, the cell used in the method of the present invention is a yeast cell, preferably wherein said cell is a *Saccharomyces* cell, more preferably wherein said cell is a *Saccharomyces cerevisiae* cell, in particular wherein said cell is derived from a *Saccharomyces cerevisiae* cell of the strain AH22.

Preferred cells of the present invention are characterized in detail above.

In a further preferred embodiment, the step of inserting a gene coding for soluble HMG-CoA reductase into a yeastl cell comprises the insertion of a vector coding for soluble HMG-CoA reductase, wherein the expression of said soluble HMG-CoA reductase is under the control of a promoter active in said cell, preferably a constitutive promoter, in particular a strong constitutive promoter.

In a further preferred embodiment, the one or more gene(s) coding for steryl acyltransferase(s) is/are ARE1 and/or ARE2, preferably wherein both genes, ARE1 and ARE2, are defective or deleted.

A third aspect of the present invention relates to the use of the cell of the present invention for the production of one or more terpene(s), preferably for the production of one or more triterpene(s), in particular for the production of squalene.

As used herein, the term "production" may refer to any means for obtaining terpenes. The production may include production at any scale. Production may include production at laboratory scale, i.e., production of several micrograms, several milligrams, or several grams of terpene(s). Production may include production at semi-technical scale, i.e., production of several grams or several kilograms of terpene(s). Further production may include production at industrial scale, i.e., production of several kilograms or tons of terpene(s). The production may further include one or more further technical step(s) for purification or conservation of the terpene(s).

As most terpenes are highly hydrophobic, the terpene(s) are typically accumulated in the cells. In a first step, the cells may be harvested by any means in the art such as, e.g., centrifugation, filtration, crossflow filtration, chromatography (e.g., affinity, size exclusion, ion-exchange chromatography), or abrasion or swabbing from a solid surface or culture plate. Then, a cell pellet may be obtained by any means, preferably by centrifugation, filtration or crossflow filtration. Alternatively, the cells may decent over time or may float due to gassing of the container comprising said cells. Optionally, the cells are washed by any means known in the art such as, e.g, by centrifugation, filtration or crossflow filtration. The cell pellet may be dried or may be not dried. The cells may be lysed by any means known in the art. The cells may be lysed by mechanical force (e.g., by homogenization (e.g., by a Potter or a Downs homogenisator), by means of a cell press such as, e.g., a French press), by detergents, by sonication, or by lytic phages. Optionally, the terpene(s) may be extracted by solvent extraction, e.g., with an organic solvent. Optionally, the organic solvent may be evaporated subsequently. Alternatively or additionally, the terpene(s) may be isolated, depending on their specific chemical nature, by chromatographic methods (e.g., phase chromatography, ion-exchange chromatography, reverse phase chromatography, size exclusion chromatography, high performance liquid chromatography (HPLC), ultrahigh pressure liquid chromatography (UPLC), fast protein chromatography (FPLC)), by electrophoresis, capillary electrophoresis (CE), or by distillation.

A further aspect of the present invention relates to a method for the production of one or more terperne(s), preferably triterpene(s), more in particular squalene, said method comprising:
 a.) cultivating the cells of the present invention in a suitable culture medium; and
 b.) isolating one or more terpene(s), preferably one or more triterpene(s), more in particular squalene from the cells or the cell culture of step a.).

It will be understood by a person skilled in the art, that for efficient production of terpene(s), the cells have to be cultivated for at least several hours, preferably for at least 12 h, more preferably for at least 24 h, even more preferably for at least 48 h or at least 72 h or even longer. The cells maybe cultivated for several generations. The cells may be cultivated for more than 5 generations, for more than 10 generations, for more than 15 generations, for more than 20 generations, for more than 25 generations, for more than 30 generations, for more than 35 generations, for more than 50 generations, for more than 100 generation, or even longer. A suspension culture may be stirred or shaken.

As used herein, the term "isolating one or more terpene(s)" may be understood in the broadest sense as the purification of the terpene(s) from the culture broth. The terpene(s) may be accumulated in the cells or may be secreted by the cells and, therefore, present in the culture medium.

The cells are harvested and optionally washed as described above. Subsequently, the cells may be lysed by any means known in the art and indicated above. Optionally, the terpene(s) may be extracted by solvent extraction, e.g., with an organic solvent. Optionally, the organic solvent may be evaporated subsequently. Alternatively or additionally, the terpene(s) may be isolated, depending on their specific chemical nature, by chromatographic methods (e.g., phase chromatography, ion-exchange chromatography, reverse phase chromatography, size exclusion chromatography, high performance liquid chromatography (HPLC), ultrahigh pressure liquid chromatography (UPLC), fast protein chromatography (FPLC)), by electrophoresis, capillary electrophoresis (CE), or by distillation.

A further aspect of the present invention relates to a method for the production of a pharmaceutical or cosmetically composition, a lubricant or transformer oil, in particular for the production of a vaccine composition, said method comprising:

a.) producing one or more terpene(s) according to the present invention; and b.) admixing said terpene(s) to said pharmaceutical or cosmetically composition, said lubricant or said transformer oil, in particular to said vaccine composition; wherein said one or more terpene(s) is/are optionally further subject to one or more hydrogenating step(s), wherein said one or more terpene(s) is/are preferably hydrogenated triterpene(s), in particular squalane.

The term "admixing" may be understood in the broadest sense as the addition of the terpene(s) to a composition of interest.

A pharmaceutical composition may refer to any pharmaceutical composition that comprises a terpene obtainable by a cell of the present invention. In a pharmaceutical composition, the terpene may preferably be used as adjuvant, as skin moistener, as mucolytic agent, as hormone, as fragrance, as lubricant, as antimicrobial agent, as anti-inflammatory agent, or as antioxidant.

A cosmetically composition may refer to any cosmetically composition that comprises a terpene obtainable by the cell of the present invention. In a cosmetically composition, the terpene may preferably used as skin moistener, as fragrance, or as antioxidant. The terpene may also be used as food additive. Further, the terpene may be used as pheromone (e.g., insect pheromone for pest control), as hormone (e.g., insect pheromone for pest control), as lubricant, as electric insulator, as transformer oil or transformer oil additive, and as raw chemical in chemical, pharmaceutical and cosmetic industry.

Preferably, the terpene obtained by the method of the present invention is squalene. Squalene may be preferably used as additive in pharmaceutical and cosmetically compositions, as skin moistener, as lubricant, as transformer oil or transformer oil additive, and as raw chemical in chemistry industry. More preferably, squalene obtained by the method of the present invention may be used in pharmaceutical and cosmetic compositions, in particular in the preparation of an emulsion that can be used as a vaccine adjuvant.

The terpene may be used for the production of one or more hydrogenated terpene(s), preferably one or more hydrogenated triterpene(s). In particular, squalane may be used for the production of squalane. For this purpose, squalene may be subject to one or more hydrogenating step(s) by any means known in the art.

As used herein, the term "hydrogenating step" refers to the hydrogenation of one or more double or triple bonds, preferably one or more double bonds, in particular one or more double bonds between carbon atoms of a terpene by the addition of hydrogen. Exemplarily, a terpene may be hydrogenated by means of a catalytic converter (e.g., platinum-, palladium-, rhodium-, nickel-, iridium- and/or ruthenium-based catalysts), gassing with hydrogen or a hydrogen-containing mixture of gasses, reaction with reducing agents such as, e.g., sodium borohydride, an enzymatic process (e.g., by a nicotinamide adenine dinucleotide- (NADH-) and/or a nicotinamide adenine dinucleotide phosphate- (NADPH-) converting enzyme(s)) or a combination of two or more thereof. The NADH- and/or NADPH-converting enzyme/s) may also be cloned into the genome of a cell of the present invention. Preferably, in a hydrogenated terpene, the most or even all double and/or triple bonds of the terpene molecule are hydrogenated, more preferably all double and/or triple bonds of the terpene molecule are hydrogenated. Preferably, the hydrogenated terpene is a hydrogenated triterpene, more preferably hydrogenated squalane. Most preferably, the hydrogenated terpene is squalane. Squalane may preferably be used in a cosmetic or a pharmaceutical composition, in particular in a cosmetic product.

BRIEF DESCRIPTION OF THE DRAWINGS

FIG. 7 shows the results of a cultivation of strain AH22tH3ura8Δare1Δare2HUL in a laboratory-scale fermenter (5 liters).

EXAMPLES

The following examples as well as the accompanying figures are intended to provide illustrative embodiments of the present invention described and claims herein. These examples are not intended to provide any limitation on the scope of the invented subject-matter.

Example 1

Construction of Strain AH22tH3ura8Δare1Δare2

1.1 Basis Strain AH22tH3ura8 (Polakowski et al., 1998)

AH22tH3ura8 is based on strain AH22 (Hinnen et al., 1978) which is a derivate of S288c (Mortimer and Johnston, 1986). The strain S288c and the strain AH22 can be obtained from the American Type Culture Collection (ATCC). The strain S288c is obtainable from the ATCC under ATCC number 26108. The strain AH22 is obtainable from the ATCC under ATCC number: 38626.

The AH22 is characterized as follows:
genotype: MATa leu2-3 leu2-112 his4-519 can1
phenotype: leu2, his4

The strain AH22 of the yeast *Saccharomyces cerevisiae* belongs to the group of microorganisms generally recognized as safe (biosafety level 1). Glycerol stocks of strain AH22 were prepared.

The strain AH22tH3ura8 was constructed by integrating a tHMG1 expression cassette into the URA3 locus (Polakowski et al., 1998). This expression cassette comprises a truncated, constitutive version of the ADH1 promoter, a truncated version of the HMG 1 gene and the TRP1 terminator (see below for construction details).

The AH22tH3ura8 strain is characterized as follows:
genotype: MATa leu2-3 leu2-112 his4-519 can1 ura3:: tHMG1
phenotype: ura3, leu2, his4

Figure 1:
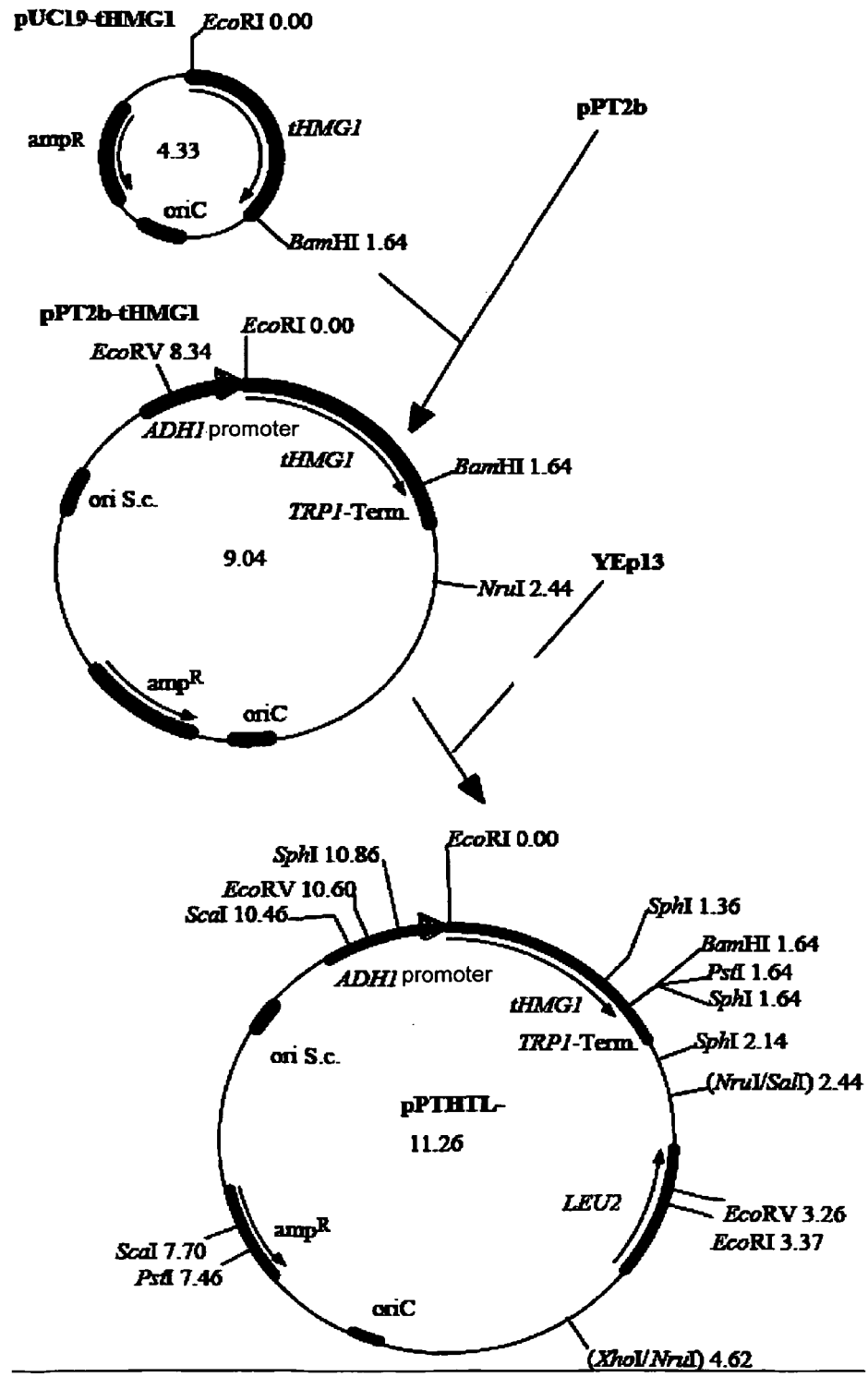
FIG. 1 shows the cloning strategy for vector pPTHTL. The HMG1 fragment from pUC19-tHMG1 is excised by EcoR1 and BamHI and is integrated in the plasmid pT2b cleaved with EcoR1 and BamHI. The LEU2 gene is cloned as blunt end fragment. Therefore, YEp13 was cleaved with XhoI and SalI and the sticky ends were filed. pPT2b-tHMG1 was opened by NruI.

1.2 Integration of the tHMG1 Expression Cassette into Locus ura3 (Cloning Strategy and Integration)
Cloning Strategy for Vector pPTHTL The DNA sequence for tHMG1 (Basson et al., 1988) was amplified via PCR from genomic DNA of *Saccharomyces cerevisiae* strain S288c (Mortimer and Johnston, 1986) with use of standard methods. The primers that were used for this purpose are the DNA oligomers tHMG-5' and tHMG-3' (Table 1). The DNA-fragment that was obtained (SEQ ID NO:2) was introduced into the SmaI site of cloning vector pUC19 (Yanisch-Perron et al., 1985) after a Klenow treatment, and yielded vector pUC19-tHMG1 (see FIG. 1).

After plasmid isolation and restriction of pUC19-tHMG1 with endonucleases EcoR1 and BamH1, the obtained fragment was introduced into yeast expression vector pPT2b (Lang and Looman, 1995), which was also treated with EcoR1 and BamH1. The resulting plasmid pPT2b-tHMG 1 contains the truncated ADH 1-promoter (Bennetzen and Hall, 1982) and the TRP1-terminator (Tschumper and Carbon, 1980) and in between the tHMG1 coding region. The LEU2 gene was excised from yeast vector YEp13 (Parent et al., 1985) with XhoI and SalI and ligated blunt end into vector pPT2b-tHMG 1 (containing the so-called medium-length ADH1-promoter, the tHMG1 gene and the TRP1-terminator) restricted with Nru1 resulting in Vector pPTHTL (see FIG. 1).
Cloning Strategy for Vector YEpH2

Figure 2:
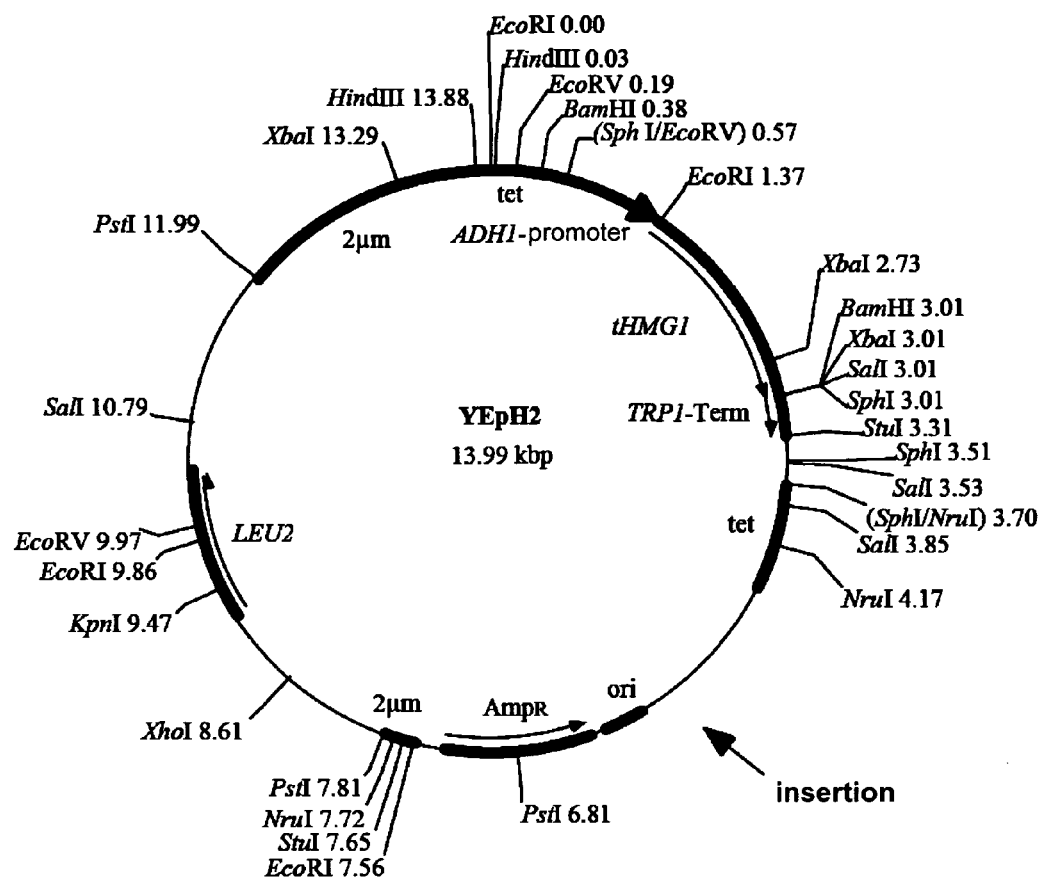
FIG. 2 shows the schematic depiction of vector YEpH2. The expression cassette of pPT2b-tHMG 1 as EcoRV/NruI fragment is ligated into Yep 13 opened and filled with SphI.

Vector YEpH2 (see FIG. 2) was constructed by blunt end ligation of the linearized (with SphI) vector YEp13 with the tHMG1 expression cassette (shorter form of ADH1 promoter; downstream of EcoRV site, Bennetzen and Hall, 1982) cut out from vector pPT2b-tHMG1 (FIG. 1) with EcoRV and NruI.
Cloning Strategy for the Integrative Vector YDpUHK3

Figure 3:
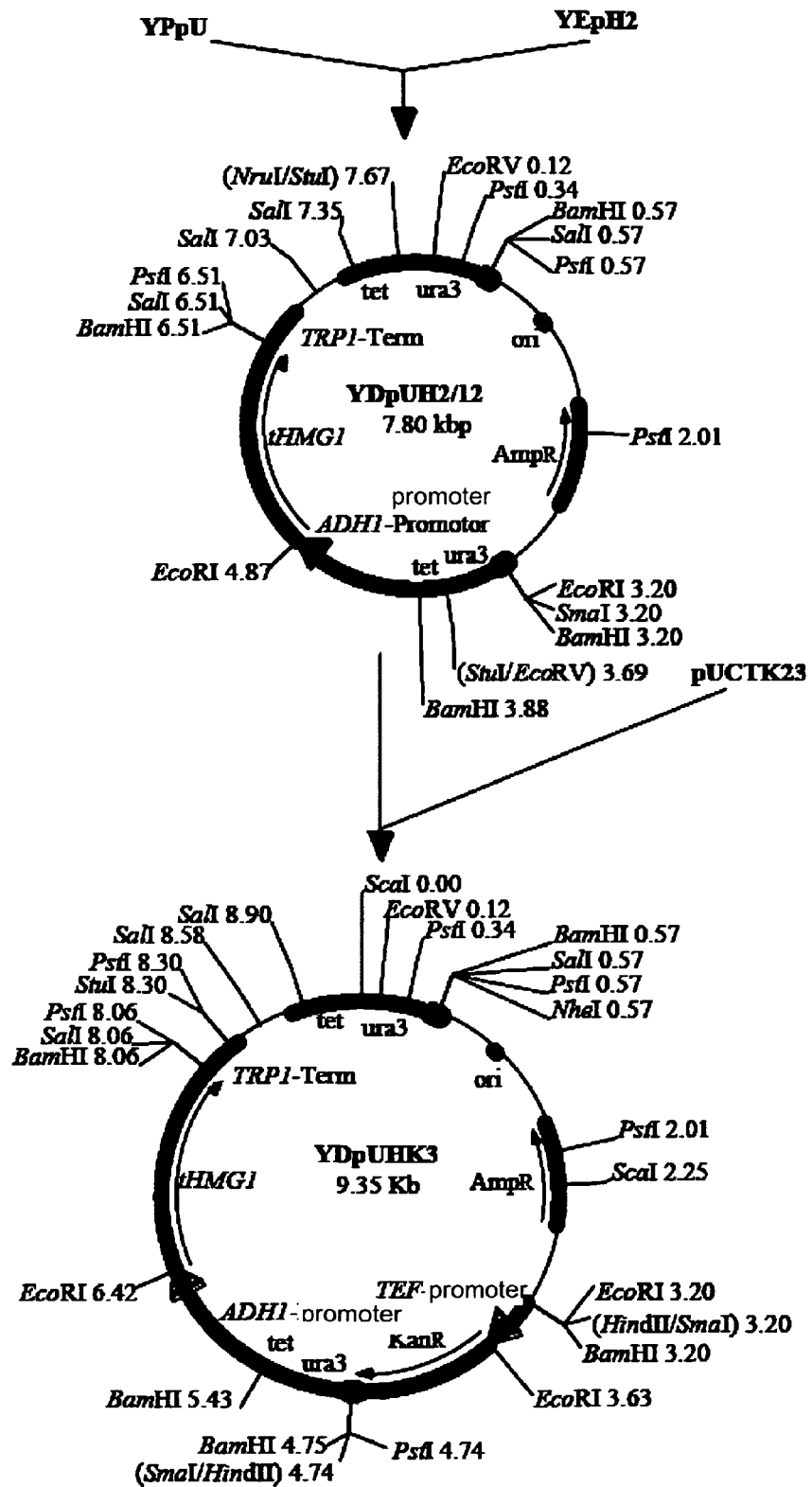
FIG. 3 shows the cloning strategy for the integrative vector YDpUHK3. The expression cassette as EcoRV/NruI fragment from YEpH2 is ligated in YDpU cleaved with StuI. The HindIII fragment from pUCTK23 is ligated with YDpUH2/12 cleaved with SmaI.
Figure 4:
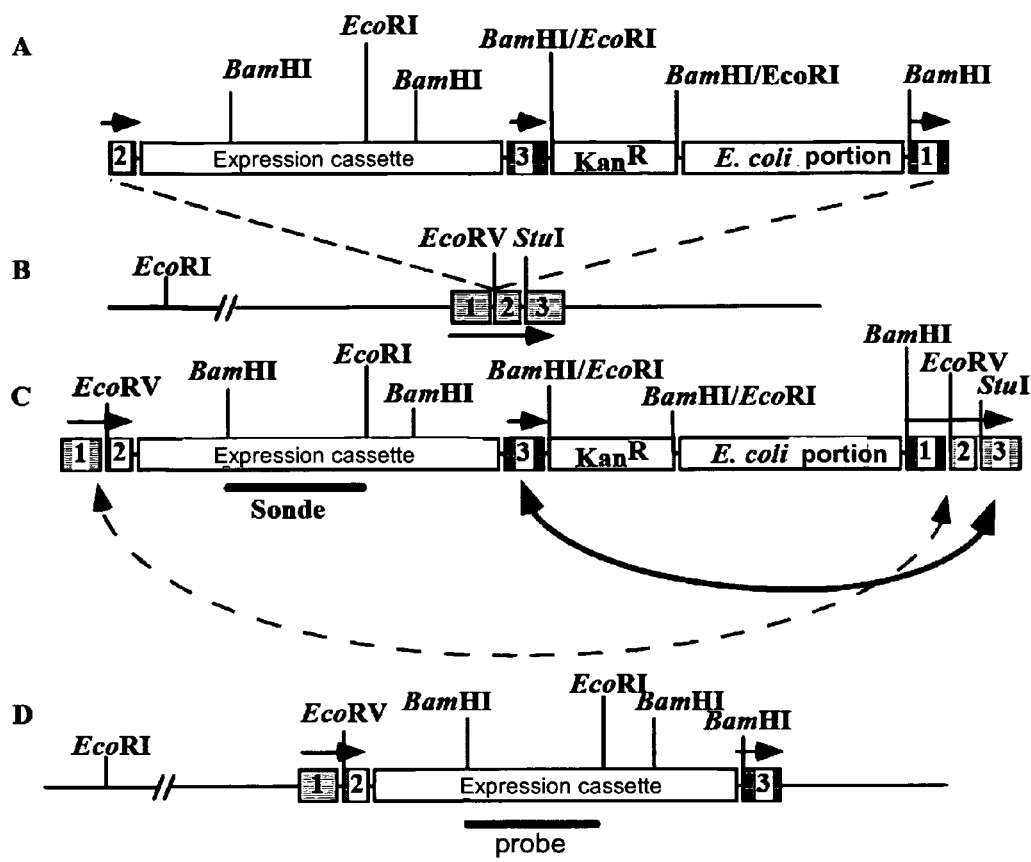
FIG. 4 shows the schematic depiction of the tHMG 1 expression cassette integrated into locus URA3 (hatched). Vector YDpUHK3 linearized with EcoRV (A) is integrated into the chromosomal URA3 gene (B). The plasmid integrates as single integration (C) or as tandem repeat. Via homologous recombination either the whole vector is lost (dashed arrow) or a part of the plasmid is lost (continuous arrow). If the expression cassette remains, the situation shown under D is implemented at the URA3 locus.

The tHMG1 expression cassette cut from vector YEpH2 (see FIG. 2) with EcoRV and NruI was introduced (ligated) into vector YDpU (Berben et al., 1991)), which was treated with Stu1. The resulting vector YDpUH2/12 (see FIG. 3) was treated with endonuclease SmaI and ligated with a HindIII fragment of vector pUCTK23 coding for kanamycin resistance (Webster and Dickson, 1983). The construct that is produced (YDpUHK3, see FIG. 3) was treated with EcoRV prior to yeast transformation. The yeast strain *Saccharomyces cerevisiae* AH22 (Hinnen et al., 1978) was transformed with this construct via the lithium acetate method described by Gietz et al. (Gietz, D., et al., 1992). The transformation of the yeast with this linearized vector results in a chromosomal integration of the total vector at the URA3 gene locus (see FIG. 4). To eliminate the areas from the integrated vector that are not part of the expression cassette (*E. coli* origin, *E. coli*-ampicillin resistance gene, TEF-promoter and kanamycin resistance gene), transformed yeasts were subjected to selection pressure by 5-FOA (Boeke et al., 1987) that promotes uracil-auxotrophic yeasts. The uracil-auxotrophic strain that was selected on plates containing 5-FOA (AH22tH3ura8) exhibits the tHMG1-expression cassette as chromosomal integration in the URA3 locus (see FIG. 4).

SEQ ID NO:3 represents the sequence of tHMG1 expression cassette integrated into URA3 locus in strain AH22tH3ura8 (including URA3 coding regions (see FIG. 4D)).

1.3. Deletion of the Genes ARE1, ARE2 in Strain AH22tH3ura8

Figure 5:
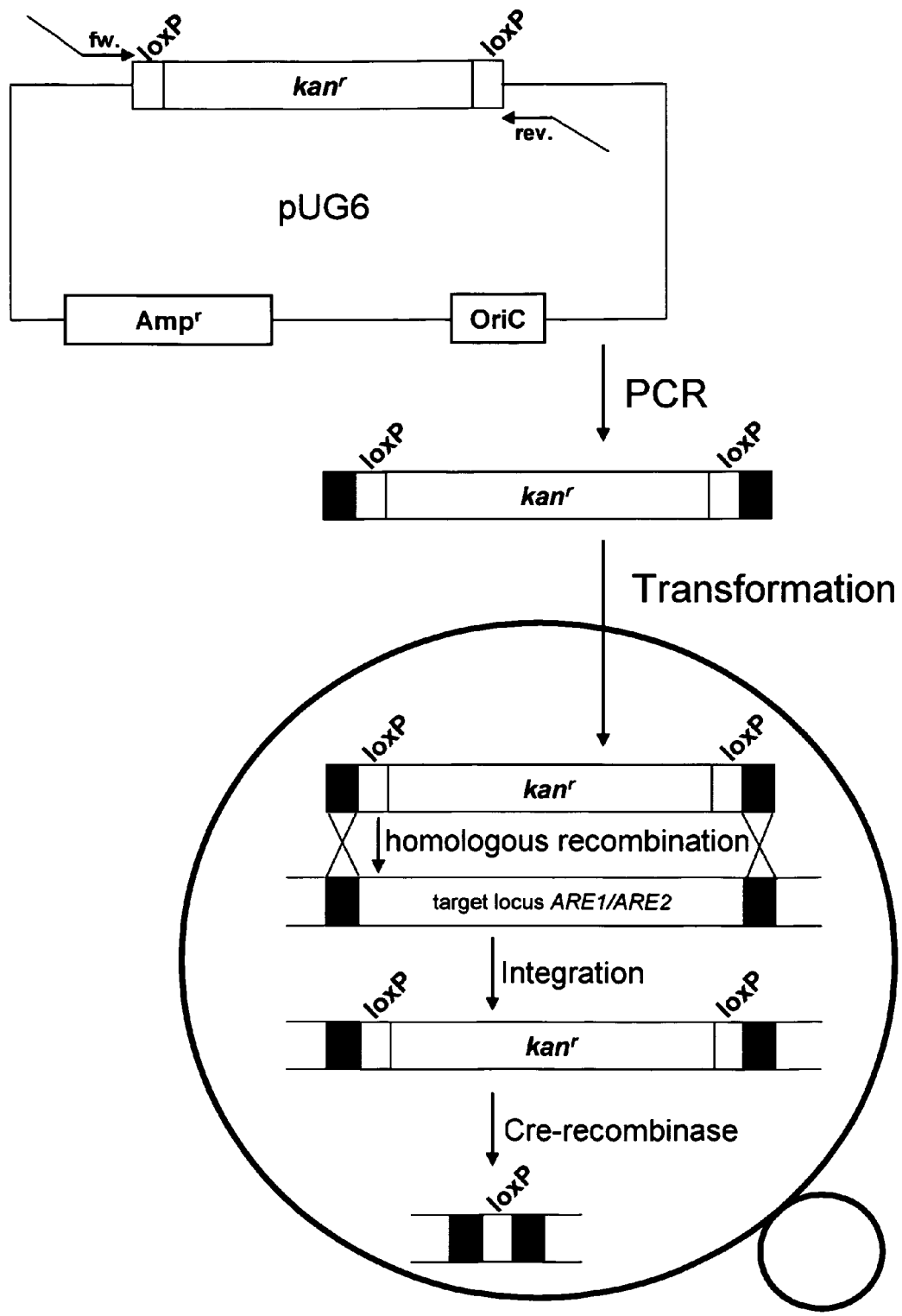
FIG. 5 shows the schematic depiction of the procedure, which was used to delete the genes ARE1, ARE2 in strain AH22tH3ura8
Figure 6A:
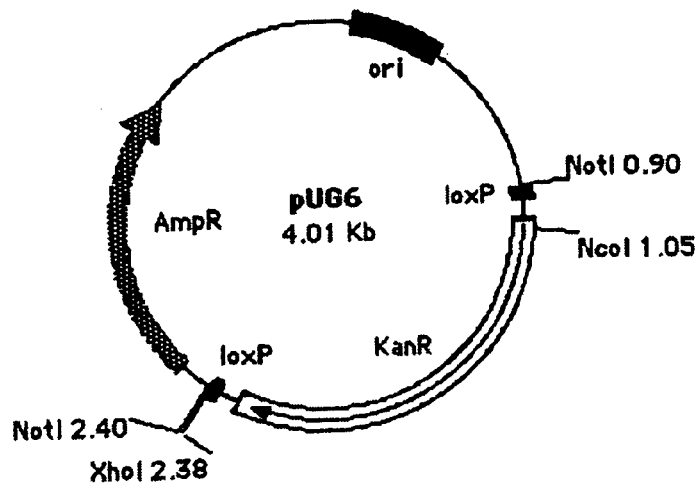
FIG. 6 shows the schematic depiction of plasmids pUG6 (FIG. 6A) and pSH47 (FIG. 6B).
Figure 6B:
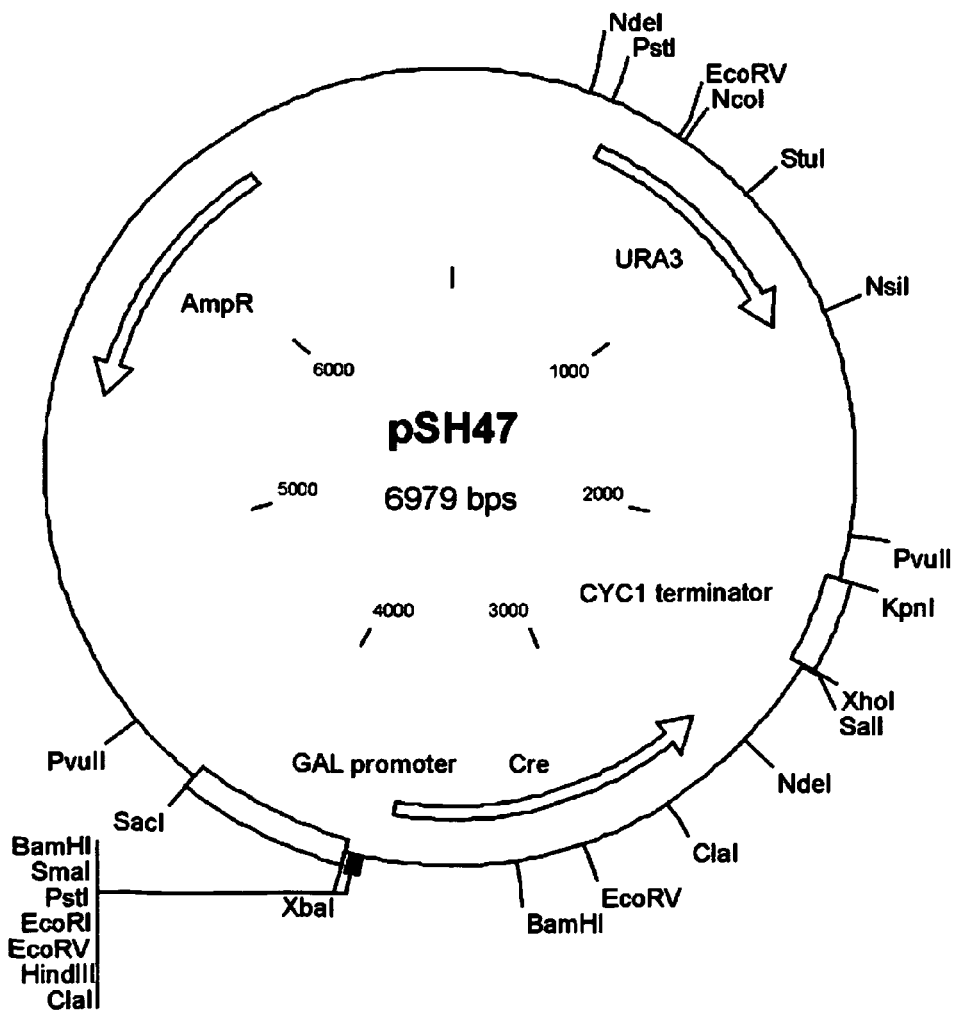

The deletion cassette with the kanMX marker gene (coding for geniticin resistance) was amplified from the plasmid pUG6 (Guldener et al., 1996) (see FIG. 6) with primers (are1crelox forward (fw), are1crelox reverse (rev) and are2crelox fw, are2crelox rev, respectively; Table 1) introducing short flanking sequences, which are homologous to the target locus ARE1 and ARE2 (see FIG. 5). The deletion cassettes (sequences of SEQ ID NO:4 and SEQ ID NO:5) were transformed into yeast via the lithium acetate method described by Gietz et al. (Gietz, D., et al., 1992).

After integration of the cassette into the target locus, which leads to a loss of the corresponding gene, the marker gene kanMX was recovered by the cre-recombinase procedure (Guldener et al., 1996) in order to be able to reuse this marker for further chromosomal deletions or integrations, respectively.

The cre-recombinase procedure requires the transformation of the yeast strains with the plasmid pSH47 (see FIG. 6), which carries the gene for the enzyme cre-recombinase. This enzyme is able to recombine the two loxP sites flanking the kanMX resistance gene. This recombination event leads to a loss of this marker gene leaving one loxP site at the target locus.

Colonies, which have lost the plasmid pSH47 were identified via counter-selection on plates with 5-fluoroorotic acid (Guldener et al., 1996) and picked for further construction purposes or as final strains.

TABLE 1

Oligonucleotides (primer) used to construct strain AH22tH3ura8Δare1Δare2

| Number | Name | Sequence |
|---|---|---|
| 1 | tHMG-5' | ACTATGGACCAATTGGTGAAAACTG |
| 2 | tHMG-3' | AGTCACATGGTGCTGTTGTGCTT |
| 3 | are1 crelox fw | ATGACGGAGACTAAGGATTTGTTGCAAGACG AAGAGTTTCccagctgaagcttcgtacgc |
| 4 | are1 crelox rev | TCATAAGGTCAGGTACAACGTCATAATGATAC TGGGCCCTgcataggccactagtggatctg |
| 5 | are2crelox fw | ATGGACAAGAAGAAGGATCTACTGGAGAACG AACAATTTCccagctgaagcttcgtacgc |
| 6 | are2crelox rev | TTAGAATGTCAAGTACAACGTACACATGACAC TTGGTCCCgcataggccactagtggatctg |

10 Glycerol stocks of strain AH22tH3ura8Δare1Δare2 were prepared. The capital letters in table 1 represent the homologous areas of the target loci, in which the respective integrative gene cassette is integrated/has been integrated.

These areas may be responsible for the chromosomal integration of the gene cassettes in the target loci (via homologous recombination; e.g., ARE1 and ARE2, respectively). Thus, these areas may be located at the beginning and the end of an integration cassette.

Example 2

Figure 8:
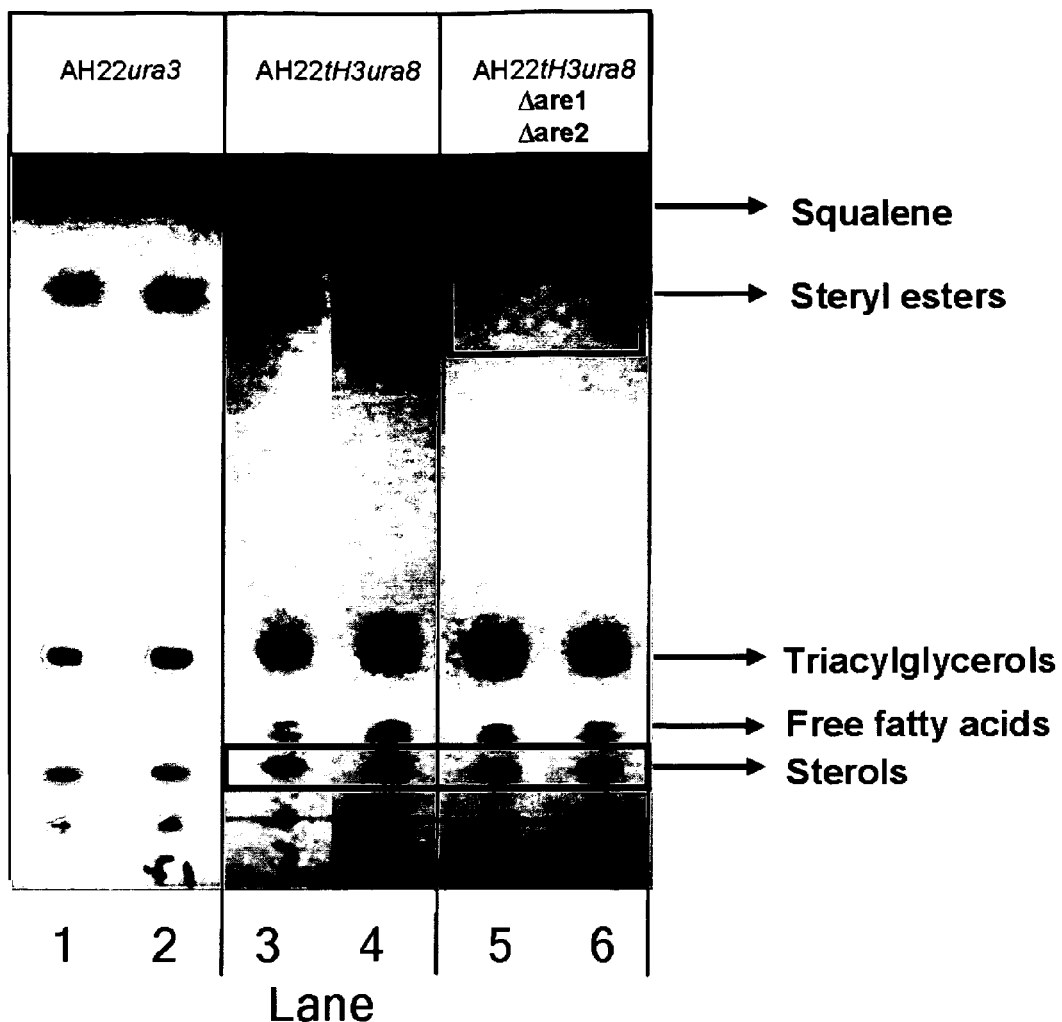
FIG. 8 shows a thin layer chromatography of whole lipid extracts from constructed mutant strains of the yeast *Saccharomyces cerevisiae*.

The neutral lipid composition and the free sterols of the constructed strains were evaluated via thin layer chromatography (TLC). Whole lipid extraction and thin layer chromatography was performed according to the protocol below.
TLC (Thin Layer Chromatography) Analysis:
Cultivation Procedure:
The cultivation procedure of strains of the yeast *Saccharomyces cerevisiae* for TLC analysis was:
Preculture:
20 ml of WMVIII medium in a 100 ml shaking flask are inoculated with 50 μl of the corresponding glycerol stock and cultivated for 48 h at 30° C. and 150 rpm.
Main Culture:
50 ml of WMVIII medium in a 250 ml shaking flask with baffles are inoculated with 1% of the preculture and cultivated for 72 h at 30° C. and 150 rpm.
Sample Preparation:
3×0.5 mL of culture broth were harvested in Eppendorf tubes (triplicates) and pelleted via centrifugation at 4000 rpm, 5 min. The supernatant is discarded. The yeast pellets were resuspended in 200 μL TE-buffer (pH=8.0). 200 μL glass beads and 200 μL chloroform/methanol (80:20 (Vol.-%)) was added.
The samples were vortexed for 5×1 min (in between cooled on ice). A hole was made in the bottom of the Eppendorf tube with a needle. The reaction tube was put in another 1.5 ml Eppendorf tube and centrifuge (1000 g for 2 min). The upper Eppendorf tube with the glass beads was discarded. The lower Eppendorf tube was closed and centrifuged (13,000 g, 15 min). During centrifugation a phase on top and below the pellet is formed. The lower organic was transferred into a 1.5 ml Eppendorf tube and analyzed via thin layer chromatography.
TLC (Thin Layer Chromatography):
Stationary phase: silica gel 60 F254, 10×20 cm, thickness of the silica layer 0.2 mm.
Mobile phase: petrolether: diethylether: acetic acid (90:10:1 (Vol. %))
Sample amount: 10 μL
Run time: until 1 cm below the top of the plate.
Detection: staining with iodine vapor (detection of squalen, triacylglycerols, sterols and steryl-esters).
Results:
FIG. 8 shows the whole/neutral lipid composition of the wildtype strain AH22ura3, the strain with the deregulated HMG-CoA Reductase AH22tH3ura8 and the double deletion strain AH22tH3ura8Δare1Δare2. FIG. 8 indicates that the wildtype strain (AH22ura3, lane 1 and 2) produced very low amounts of squalene in comparison to the strains in lane 3 to 6, which express the deregulated HMG-CoA reductase and produce high amounts of squalene. The deletion of the genes encoding for the enzymes responsible for the formation of steryl esters (ARE1, ARE2) resulted in a complete lack of these components in the corresponding strain (indicated by the upper black box in lane 5 to 6). The deletion of the genes encoding for the enzymes responsible for the formation of steryl esters (ARE1, ARE2) did not lead to an accumulation of free sterols (compare lane 3 and 4 with lane 5 and 6; indicated by the lower black box). This was surprising, as the content of free sterols was expected to be increased in a strain lacking the ability to store sterols as steryl esters.

The lipid components were identified via the standards squalene, cholesteryl-oleate, trioleate, oleate and ergosterol (not shown).

Example 3

Construction of Strain AH22tH3ura8Δare1Δare2—Prototrophic (Final Strain 1) and Cell Bank Manufacture and Storage 3.1. Strain Construction Details, Primer and Sequencing
Construction of Strain AH22tH3ura8Δare1Δare2H (Intermediate Strain 1):
A HIS4 prototrophic clone (revertant) of strain AH22tH3ura8Δare1Δare2 was selected on a plate lacking histidine after streaking out a liquid culture of AH22tH3ura8Δare1Δare2 with an inoculating loop (see below).
Construction of Strain AH22tH3Ura8Δare1Δare2HL (Intermediate Strain 2):
The coding region of the gene LEU2 was amplified from genomic DNA of strain S288c with primer 1 and primer 2 (see Table 2 for primer sequences). The resulting gene cassette was transformed into strain AH22tH3ura8Δare1Δare2 H. The correct integration into target locus LEU2 (YCL018W) via homologous recombination was checked via PCR analysis with primer 3 and primer 2 (annealing in 5' UTR region of the LEU2 locus and in the LEU2 coding region; see Table 2 for primer sequences).
Construction of Strain AH22tH3ura8Δare1Δare2HUL (Final Strain 1):
The complete native expression cassette of the gene URA3 (including the native promoter and terminator) was amplified from genomic DNA of strain S288c with primer primer 4 and primer 5 introducing 5'- and 3'-overhanging sequences (40 bp in length), which are homologous to the target integration locus. The native locus of the gene URA3 was not used as target locus, because the tHMG expression cassette is integrated into this locus in strain AH22tH3ura8Δare1Δare2HL. As alternative chromosomal expression locus the HO locus was chosen. The native URA3 expression cassette (including the native promoter and terminator) was transformed into strain AH22tH3ura8Δare1Δare2 HL. The correct integration into target locus HO (YDL227C) via homologous recombination was checked via PCR analysis with primer 6 and primer 7 (annealing in 5' UTR region and 3' UTR region of the HO locus; see Table 2 for primer sequences).
Sequencing:
The reversion of the mutation his4-519 (frame shift mutation, contains base insertion resulting in 5'-GGGG-3' mRNA sequence in place of wildtype 5'-CCC-3' glycine codon (Gaber and Culbertson, 1982)) was proven via sequencing of a PCR amplification product, which was generated by amplifying the corresponding HIS3 coding sequence from genomic DNA of strain AH22tH3ura8Δare1Δare2HUL with primer 8 and primer 9 (annealing in the middle of the HIS4 coding region and in 3' UTR region of the HIS4 locus; see Table 2 for primer sequences).
Result: Sequence is correct (corresponds to sequence of S288c, which is deposited at the *Saccharomyces* Genome Database (SGD). Reversion of mutation his4-519 occurred. In case of the his4-519 mutation, reversion of the histidine auxotrophy phenotype can also occur via an extragenic suppressor mutation in glycine tRNA (Gaber and Culbertson, 1982).

The correct sequence of the LEU2 coding region at the LEU2 Locus (YCL018W) in strain AH22tH3ura8Δare1Δare2HUL was proven via sequencing a PCR amplification product, which was generated by amplifying the whole LEU2 coding sequence including a part of the 5' UTR of the LEU2 locus from genomic DNA of strain AH22tH3ura8Δare1Δare2HUL with primer 3 and primer 2 (see Table 2 for primer sequences).

Result:

Sequence is correct (corresponds to sequence of S288c, which is deposited at *Saccharomyces* Genome Database (SGD).

The correct sequence of the native expression cassette of the gene URA3 (including the native promoter and terminator) integrated into the HO locus (YDL227C) in strain AH22tH3ura8Δare1Δare2HUL was proven via sequencing a PCR amplification product, which was generated by amplifying the expression cassette of the gene URA3 from genomic DNA of strain AH22tH3ura8Δare1Δare2HUL with primer 6 and primer 7 (annealing in 5' UTR region and 3' UTR region of the HO locus; see Table 2 for primer sequences).

Result:

Sequence is correct (corresponds to sequence of S288c, which is deposited at *Saccharomyces* Genome Database (SGD).

TABLE 2

Oligonucleotides (primer) used to construct strain AH22tH3ura8Δare1Δare2HUL

| Number | Name | Sequence |
|---|---|---|
| 1 | LEU2 fw | ATGTCTGCCCCTAAGAAGATC |
| 2 | LEU2 rev | TTAAGCAAGGATTTTCTTAACTTC |
| 3 | 5' LEU2 fw | GGTGGTTAGCAATCGTCTTAC |
| 4 | ho::URA3 fw | ATGCTTTCTGAAAACACGACTATTCTGATGGC TAACGGTGAATGTGGCTGTGGTTTCAGGGTC |
| 5 | ho::URA3 rev | TTAGCAGATGCGCGCACCTGCGTTGTTACCAC AACTCTTATCCTTTTTATAAAGGCCATGAAGC |
| 6 | 5' HO fw | CATAAGCAGCAATCAATTCTATC |
| 7 | 3' HO rev | ATTTCTACTCCAGCATTCTAG |
| 8 | HIS4 fw. middle | TCTGAATATGAAGCATCTGAAG |
| 9 | 3' HIS4 rev. | ATGGCGCTAATGTCTTCAATAC |

3.2 Preparation of Glycerol Stocks of Intermediate Strain 1 AH22tH3ura8Δare1Δare2H WMVIII medium was prepared as shown by Lang and Looman (Lang and Loomann, 1995).

Strain AH22tH3ura8Δare1 Δare2 was inoculated with 50 μl of a glycerol stock in 20 mL WMVIII medium supplemented with uracil (100 mg/L) and leucine (400 mg/L) in a 100 mL shaking flask without baffles and incubated for 72 h at 30° C. and 150 rpm (inoculum 0).

Inoculum 0 was streaked out with an inoculating loop on a WMVIII agar plate supplemented with uracil (100 mg/L) and leucine (400 mg/L) (no histidine), which was incubated for 72 h at 30° C. (plate 1). Colony number (number of revertants) was not determined.

Inoculum 1 was inoculated with a colony picked from plate 1 in 20 mL WMVIII medium supplemented with uracil (100 mg/L) and leucine (400 mg/L) in a 100 mL shaking flask without baffles and incubated for 72 h at 30° C. and 150 rpm (inoculum 1).

Inoculum 2 was inoculated with 350 μL of inoculum 1 in 35 mL WMVIII medium supplemented with uracil (100 mg/L) and leucine (400 mg/L) in a 100 mL shaking flask without baffles and incubated for 48 h at 30° C. and 150 rpm (inoculum 2).

Inoculum 2 was used to prepare glycerol stocks of intermediate strain 1 (AH22tH3ura8Δare1Δare2H). The glycerol stocks were prepared by mixing 0.5 mL of inoculum 2 with 0.5 mL glycerol solution (50% (v/v) glycerol in water). 10 glycerol stocks of intermediate strain 1 (AH22tH3ura8Δare1Δare2H could be transported on dry ice.

Testing of Inoculum 2:

a) Optical Density of Inoculum 2:
   OD600/mL: 39.44 b) Viability of Cells of Inoculum 2 (Before Preparation of Glycerol Stocks):

The viability of the cells of inoculum 2 in % was calculated by dividing the colony forming units by the cell number (×100). The cell number was determined via counting in a Thoma counting chamber. The colony forming units were determined by streaking out an appropriate dilution of inoculum 2 on a WMVIII agar plate supplemented with uracil (100 mg/L) and leucine (400 mg/L).

c.) Thoma Counting Chamber: 1:10 Dilution of Inoculum 2
1. counting: 34; 31; 38; 32; 39
2. counting: 31; 37; 31; 33; 31
33.7 cells×$1.25×10^6$×10=$4.2×10^8$ cells/mL inoculum 2 d.) Colonies on Plate:

50 μl of a 10-5 dilution of inoculum 2 plated on a WMVIII plate counted: 207 colonies×$10^5$×20=$4.14×10^8$ colonies/mL inoculum 2 viability: $4.1×10^8$×100/$4.2×10^8$→98.6%

Viability of Cells of Inoculum 2: 98.6% e.) Purity and Phenotype:

TABLE 3

50 μl of inoculum 2 (diluted to $10^{-5}$ with water or undiluted as indicated) were streaked out on indicated plates and incubated for 48 h at indicated temperatures to determine purity and phenotype (auxotrophies)

| Strain (inoculum 2) | Plates | Incubation temperature | Observation |
|---|---|---|---|
| AH22tH3ura8Δare1Δare2H | YE | 30° C. | single yeast colonies (inoculum 2 was diluted $10^{-5}$ prior to streaking out on plate) |
| | WMVIII + Ura + Leu | 30° C. | single yeast colonies (inoculum 2 was diluted $10^{-5}$ prior to streaking out on plate) |
| | LB | 37° C. | no growth (undiluted) |
| | WMVIII (no amino acids) | 30° C. | no growth (undiluted) |
| | WMVIII + Ura + His | 30° C. | no growth (undiluted) |
| | WMVIII + Leu + His | 30° C. | no growth (undiluted) |

Inoculum 2 was also checked on bacterial contaminations under the microscope → No bacterial contamination could be detected.

3.3 Construction of Intermediate Strain 2 and Preparation of Glycerol Stocks of Intermediate Strain 2 AH22tH3ura8Δare1Δare2HL Construction (Technical Procedure):

Transformation and PCR proof on correct integration of LEU2 expression cassette into locus LEU2 is performed by means well-known in the art and described below.

Results of Yeast Transformation:

Transformation was carried out as described by Gietz et al. (Gietz, D., et al., 1992). Transformation efficiency (integrative transformation) varied between $10^2$-$10^3$ transformants per µg of DNA.

Sample 1 cultivated on a control plate (AH22tH3ura8Δare1 Δare2H and no DNA) leads to no colony growth. Cultivating sample 2 wherein the AH22tH3ura8Δare1Δare2H+ LEU2 cassette was inserted leads to detectable differing colonies.

15 colonies were picked on new WMV111 plate and incubated for 72 h at 30° C. Five colonies were checked by PCR. The largest colony was selected for preparation of glycerol stock. The experimental evaluation of five colonies revealed that all five colonies were usable. All five samples showed that the analyzed DNA contained the LEU2 gene.

PCR:

The template was obtained from colonies of Yeast Transformation, from the 2. inoculation on new agar plates. PuRe Taq Ready To Go-Beads (GE Healthcare: Lot: 384777) are used as Taq-polymerase in a volume of 25 µl.

This leads to solved beads in 23 µl sterile HPLC-$H_2O$ and added 1 µl of each primer fw./rev. (see Table). The used PCR-machine was obtained from Flex Cycle Analytik, Jena.

PCR-Program:
step 1: 94° C. 3 min
step 2: 94° C. 30 sec
step 3: 53° C. 30 sec
step 4: 72° C. 2 min to step 2 40 cycles
step 5: 72° C. 3 min
step 6: 4° C.

The PCR was performed with colonies 1, 2, 3, 4 and 5 of AH22tH3ura8Δare1Δare2HL and each 1 µL primer (10 µmol/µl dilution) of primers 5' LEU2 fw and LEU2 rev. The amplification product is approximately 1185 bp in length.

Gel Electrophoresis on a 1% Agarose Gel:

0.5 g Seakem LE Agarose from Biozym in 100 mL shake flask+50 mL 1×TAE-buffer 6 µL of a 1 kb ladder (NEB) (500 ng/lane) was loaded in one lane. Further 10 µL sample of each amplificate was mixed with 2 µL 6× loading buffer and the mixture was loaded on the agarose gel. The gel was run at 120 V for 45 min in 1×TAE-buffer. Subsequently, the gel was incubated in an ethidium bromide (EtBr) bath for 20 min (EtBr conc. Stock: 10 mg/mL; bath: 30 µL/300 mL 1×TAE-buffer). Finally, the gel was analyzed by photographic documentation (Alpha innotech: OrgBal 48; optional settings: exp. 0.12 s, bin 1×1, b: 0, w: 66, g: 0.95).

Results:

All 5 lanes loaded with the sample showed that the strain was a AH22tH3ura8Δare1Δare2HL strain. The five colonies showed amplified products of approximately 1200 bp. According to the gel electrophoresis, the results for all five analyzed colonies contain the correct insert. Therefore, the amplification of LEU2 gene resulted in positive results in all 5 colonies of strain AH22tH3ura8Δare1Δare2 HL Preparation of Glycerol Stocks of Strain AH22tH3Ura8Δare1Δare2HL Strain AH22tH3ura8Δare1Δare2HL was inoculated with a colony picked from a WMVIII agar plate supplemented with uracil (100 mg/L) (plate 1; see below; not equal to transformation plate) in 20 mL WMVIII medium supplemented with uracil (100 mg/L) in a 100 mL shaking flask without baffles and incubated for 72 h at 30° C. and 150 rpm (inoculum 1).

Plate 1 was generated by picking single colonies from the transformation plate (see FIG. 1), which was generated by transforming strain AH22tH3ura8Δare1Δare2H with a DNA fragment comprising the LEU2 coding sequence. Plate one, not the transformation plate, was used for the further procedure.

Inoculum 2 was inoculated with 350 µL of inoculum 1 in 35 mL WMVIII medium supplemented with uracil (100 mg/L) in a 100 mL shaking flask without baffles and incubated for 48 h at 30° C. and 150 rpm (inoculum 2).

Inoculum 2 was used to prepare glycerol stocks of intermediate strain 2 (AH22tH3ura8Δare1Δare2HL). The glycerol stocks were prepared by mixing 0.5 mL of inoculum 2 with 0.5 mL glycerol solution (50% (v/v) glycerol in water). 10 glycerol stocks could be transported on dry ice.

Testing of Inoculum 2:

a) Optical Density of Inoculum 2:
OD600/ml: 37.04 b) Viability of Cells of Inoculum 2 (Before Preparation of Glycerol Stocks):

The viability of the cells of inoculum 2 in % was calculated by dividing the colony forming units by the cell number (×100). The cell number was determined via counting in a Thoma counting chamber. The colony forming units were determined by streaking out an appropriate dilution of inoculum 2 on a WMVIII agar plate supplemented with uracil (100 mg/L).

c.) Thoma Counting Chamber: 1:10 Dilution of Inoculum 2
1. counting: 33; 36; 32; 37; 39
2. counting: 28; 37; 41; 33; 31
34.7 cells×$1.25×10^6$×10=$4.3×10^8$ cells/mL of inoculum 2 d.) Colonies on Plate:

50 µl of a $10^{-5}$ fold dilution of inoculum 2 plated on a WMVIII plate resulted in:
counted 142 colonies×$10^5$×20=$2.8×10^8$ colonies/mL of inoculum 2,
viability: $2.8×10^8$×$100/4.3×10^8$, results in 65.1%

Viability of cells of inoculum 2: 65.1% e) Purity and Phenotype:

TABLE 4

50 µl of inoculum 2 (diluted by $10^{-5}$ with water or undiluted as indicated) were streaked out on indicated plates and incubated for 48 h at indicated temperatures to determine purity and phenotype (auxotrophies).

| Strain (inoculum 2) | Plates | Incubation temperature | Observation |
|---|---|---|---|
| AH22tH3ura8Δare1ΔareHL | YE | 30° C. | single yeast colonies (inoculum 2 was diluted $10^{-5}$ prior to streaking out on plate) |
| | WMVIII + Ura | 30° C. | single yeast colonies (inoculum 2 was diluted $10^{-5}$ prior to streaking out on plate) |
| | LB | 37° C. | no growth (undiluted) |
| | WMVIII (no amino acids) | 30° C. | no growth (undiluted) |

Inoculum 2 was also checked on bacterial contaminations under the microscope. No bacterial contamination could be detected.

3.4. Construction of Final Strain I and Preparation of Glycerol Stocks of Final Strain 1 AH22tH3ura8Δare1Δare2HUL Construction (Technical Procedure):

Transformation and PCR proof on correct integration of URA3 expression cassette into locus HO.

Results of Yeast Transformation:

Transformation was carried out as described by Gietz et al. (Gietz, D., et al., 1992).

Transformation efficiency (integrative transformation) varied between $10^2$-$10^3$ transformants per μg of DNA.

Cultivation of sample 1 leads to a control plate (AH22tH3ura8Δare1Δare2HL and no DNA) with no colony growth, whereas sample 2 comprising cells with the AH22tH3ura8Δare1Δare2HL+URA 3 cassette leads to the formation of differing colonies.

15 colonies were picked and seeded on new WMV111 plate and incubated for 72 h at 30° C. Positive transformants used for preparation of glycerol stocks (colony 6 and 8). Large colonies were selected picked onto another plate and checked via PCR and used for preparation of glycerol stocks.

PCR:
Template: colonies of Yeast Transformation
Yeast strain: AH22tH3ura8Δare1Δare2HUL PuRe Taq Ready To Go-Beads (GE Healthcare: Lot: 384777) was used as TAQ-polymerase in a volume of 25 μl. The beads were dissolved in 23 μl sterile HPLC-$H_2O$ and 1 μl of each primer fw./rev. (see Table 6) was added. The used PCR-machine was obtained from Flex Cycle Analytik, Jena.

PCR-Program:
1. step: 94° C. 3 min
2. step: 94° C. 30 sec
3. step: 51° C. 30 sec, new annealing temperature
4. step: 72° C. 2 min to step 2 for 40 cycles
5. step: 72° C. 3 min
6. step: 4° C.

TABLE 5 performance of PCR

| sample | strain | primer pair each direction 1 μl à 10 pmol/μl dilution |
|---|---|---|
| 1 | AH22tH3 ura8 Δare1Δare2HUL colony 1 | 5'HO fw. |
| 2 | AH22tH3 ura8 Δare1Δare2HUL colony 2 | 3'HO rev. |
| 3 | AH22tH3 ura8 Δare1Δare2HUL colony 3 | Integration of URA 3 cassette into HO locus, fragment has 1435 bp in case of correct integration, if not then 1902 bp |
| 4 | AH22tH3 ura8 Δare1Δare2HUL colony 4 | |
| 5 | AH22tH3 ura8 Δare1Δare2HUL colony 5 | |
| 6 | AH22tH3 ura8 Δare1Δare2HUL colony 6 | |
| 7 | AH22tH3 ura8 Δare1Δare2HUL colony 7 | |
| 8 | AH22tH3 ura8 Δare1Δare2HUL colony 8 | |
| 9 | AH22tH3 ura8 Δare1Δare2HUL colony 9 | |
| 10 | AH22tH3 ura8 Δare1Δare2HUL colony 10 | |
| 11 | AH22tH3 ura8 Δare1Δare2HUL colony 6 | 3'HO rev. URA 3 Not 1 fw. |
| 12 | AH22tH3 ura8 Δare1Δare2HUL colony 7 | |
| 13 | AH22tH3 ura8 Δare1Δare2HUL colony 8 | |
| 14 | AH22tH3 ura8 Δare1Δare2HUL colony 9 | |
| 15 | AH22tH3 ura8 Δare1Δare2HUL colony 10 | |

A 1% Agarose Gel was Prepared:

1.0 g Seakem LE Agarose from Biozym in 250 mL shake flask+100 mL 1×TAE-buffer. 6 μL of a 1 kb ladder (NEB) (500 ng/lane) was loaded in one lane. Further, 10 μL sample of each amplificate was mixed with 2 μL 6× loading buffer and the mixture was loaded on the agarose gel. The gel was run at 120 V for 45 min in 1×TAE-buffer. Subsequently, the gel was incubated in an ethidium bromide (EtBr) bath for 20 min (EtBr conc. Stock: 10 mg/mL: bath: 30 μL/300 mL 1×TAE-buffer). Finally, the gel was analyzed by photographic documentation.

Results:

The amplification products having the correct size of approximately 1435 bp were used further.

Preparation of Glycerol Stocks of Strain AH22tH3ura8Δare1Δare2HUL:

Strain AH22tH3ura8Δare1 Δare2HUL was inoculated with a colony picked from a WMVIII agar plate (colony 6, see FIGS. 4 and 5; plate 1; see below; not equal to transformation plate, no supplementation) in 20 mL WMVIII medium (no supplementation) in a 100 mL shaking flask without baffles and incubated for 72 h at 30° C. and 150 rpm (inoculum 1).

Plate 1 was generated by picking single colonies from the transformation plate (see FIG. 4), which was generated by transforming strain AH22tH3ura8Δare1Δare2HL with a DNA fragment comprising the native URA3 expression cassette. Plate one, not the transformation plate, was used for the further procedure.

Inoculum 2 was inoculated with 350 μL of inoculum 1 in 35 mL WMVIII medium (no supplementation) in a 100 mL shaking flask without baffles and incubated for 48 h at 30° C. and 150 rpm (inoculum 2).

Inoculum 2 was used to prepare glycerol stocks of final strain 1 (AH22tH3ura8Δare1Δare2HUL). The glycerol stocks were prepared by mixing 0.5 mL of inoculum 2 with 0.5 mL glycerol solution (50% (v/v) glycerol in water). 10 glycerol stocks could be transported on dry ice.

Testing of Inoculum 2:

a) Optical Density of Inoculum 2:
OD600/ml: 42.68 b) Viability of Cells of Inoculum 2 (Before Preparation of Glycerol Stocks):

The viability of the cells of inoculum 2 in % was calculated by dividing the colony forming units by the cell number (×100). The cell number was determined via counting in a Thoma counting chamber. The colony forming units were determined by streaking out an appropriate dilution of inoculum 2 on a WMVIII agar plate supplemented with uracil (100 mg/L).

c.) Thoma Counting Chamber: 1:10 Dilution of Inoculum 2
1. counting: 26; 29; 37; 30; 229
2. counting: 39; 36; 28; 27; 33
31.4 cells×$1.25×10^6$×15=$5.9×10^8$ cells/mL inoculum 2 d.) Colonies on Plate:
50 μl of a $10^{-5}$ dilution of inoculum 2 plated on a WMVIII plate
counted: 280 colonies×$10^5$×20=$5.6×10^8$ colonies/mL inoculum 2
viability: $5.6×10^8$×100/$5.9×10^8$. This leads to 94.9%.

Viability of cells of inoculum 2: 94.9% e) Purity and Phenotype:

TABLE 6

50 μl of inoculum 2 (diluted by $10^{-5}$ with water or undiluted as indicated) were streaked out on indicated plates and incubated for 48 h at indicated temperatures to determine purity and phenotype (auxotrophies).

| Strain (inoculum 2) | Plates | Incubation temperature | Observation |
|---|---|---|---|
| AH22tH3ura8Δare1Δare2HUL | YE | 30° C. | single yeast colonies (inoculum 2 was diluted $10^{-5}$ prior to streaking out on plate) |

TABLE 6-continued

50 µl of inoculum 2 (diluted by $10^{-5}$ with water or undiluted as indicated) were streaked out on indicated plates and incubated for 48 h at indicated temperatures to determine purity and phenotype (auxotrophies).

| Strain (inoculum 2) | Plates | Incubation temperature | Observation |
| --- | --- | --- | --- |
| | LB | 37° C. | no growth (undiluted) |
| | WMVIII (no amino acids) | 30° C. | single yeast colonies (inoculum 2 was diluted $10^{-5}$ prior to streaking out on plate) |

Inoculum 2 was also checked on bacterial contamination under the microscope. No bacterial contaminations could be detected.

3.5 Conclusions

The integrated fragments (LEU2 and URA3 expression cassette) were checked via PCR on the correct size and on correct integration at the corresponding target loci (LEU2 and HO) The PCR results showed correct sizes and correct integration of fragments.

Sequencing results of the integrated fragments (LEU2 and URA3 expression cassette) amplified from the integration locus (LEU2 and HO) of genomic DNA of final strain AH22tH3ura8Δare1Δare2HUL showed that sequences are correct (they correspond to sequences of S288c, which are deposited at *Saccharomyces* Genome Database (SGD). Reversion of mutation his4-519 occurred, as this sequence was also checked as described above in final strain AH22tH3ura8Δare1Δare2HUL. The final strain AH22tH3ura8Δare1Δare2HUL exhibits the correct phenotype (prototrophic). Construction of final prototrophic strain AH22tH3ura8Δare1Δare2HUL was successfully completed.

This strain has been successfully constructed using no heterologous gene, which then simplify the industrial implementation, in comparison with the case when strains bearing heterologous genes are used.

Example 4

Evaluation of Growth and Squalene Productivity of the Prototrophic Yeast Strain AH22tH3ura8Δare1Δare2HUL in Comparison to the Auxotrophic Yeast Strain AH22tH3ura8Δare1Δare2

Within the following experiment the growth performance and the squalene productivity of the prototrophic strain in comparison to the auxotrophic strain was evaluated.

Additionally the stability of the two strains concerning growth performance and squalene productivity over a production cycle was evaluated. Thereto glycerol stocks were prepared (post stocks) from cultures (inoculated with the initial glycerol stocks: prae stocks), which were maintained over at least 30 generations. The 30 generations represent one production cycle (cultivation in fermenter at industrial scale). After cultivating for 30 generations, the samples were tested again (post stocks). The stability concerning growth and productivity during cultivation over at least 30 generations is a preferred feature that a strain suitable for industrial production should exhibit. For evaluation of the stability cultures inoculated with prae and post stocks were evaluated in parallel.

CDW (Cell Dry Weight)—Determination:

3×6 mL of culture broth was harvested in weighted 15 mL falcon tubes (triplicates) and pelleted via centrifugation at 4000 rpm, 5 min. The supernatant was discarded and the pellet used for further analysis. The pellets are washed 2 times with 5 mL of water. The washed pellets were dried at 80° C. for 24 h and cooled in an exicator before weighing.

Extraction and Quantitative Determination of Squalene Via GC-MS Analysis:

Extraction:

250 µl of culture broth were transferred into an Eppendorf tube. The broth was vortexed (shaken) for a few seconds at maximal. speed (Vortex-Genie 2, Scientific Industries). 250 µl of glass beads (diameter ranging from 450 µm to 500 µm, Sartorius BBI-8541701) were added. Subsequently, 400 µl of chloroform:methanol (80:20; v:v) were added. The solution was vortexed for 5 minutes at maximal speed (Vortex-Genie 2, Scientific Industries) prior to centrifugation for 5 min at 13,200 rpm (Hettich Mikro 200 R laboratiory centrifuge). 50 µl of the lower organic phase were dried under nitrogen flow and the residues were solubilized in 1.5 ml of acetonitril. 1 ml of the acetonitril solution was transferred in a GC-vial and injected Preparation of External Standards for Quantification:

10 mg of squalene (Sigma, S3626, min. 98% pure) were put into a 15 ml Greiner tube. 10 ml of acetonitril were added (squalene stock solution, 1 mg/ml) and different concentrations were prepared as depicted below:

1. 5 µg/mL squalene: pipet 5 µL squalene stock solution to 995 µL acetonitrile 2. 10 µg/mL squalene: pipet 10 µL squalene stock solution to 990 µL acetonitrile 3. 20 µg/mL squalene: pipet 20 µL squalene stock solution to 980 µL acetonitrile 4. 40 µg/mL squalene: pipet 40 µL squalene stock solution to 960 µL acetonitrile 3. 80 µg/mL squalene: pipet 80 µL squalene stock solution to 920 µL acetonitrile GC-MS Analysis:

GC-MS analysis was performed on an Agilent 6890N GC system coupled to an Agilent 5975B VL MSD quadrupole mass selective detector. The column used for the analysis was an Agilent HP-5MS. The MS was operated in scan mode (start after 4 min, mass range 29 to 500 a.m.u at 3,1 scans/s). The temperature was initially held at 70° C. for 0.5 min and was then raised to 120° C. with a gradient of 20° C./min followed by a raise to 325° C. with a gradient of 10° C./min, which was held for 20 min. The flow through the column was held constant at 1 ml He/min. The injection volume was 1 µl (splitless mode). The inlet temperature and the temperature of the interface was 280° C.

4.1 Generation of Post Glycerol Stocks from Prae Glycerol Stocks after Cultivation for at Least 30 Generations:

a.) Cultivation Procedure

TABLE 7

Strains used for generation of post-stocks

| No. | Strain | Phenotype | Supplements |
|---|---|---|---|
| 1. | AH22tH3ura8Δare1Δare2HUL | prototroph | — |
| 4. | AH22tH3ura8Δare1Δare2 | auxotroph, (his ura leu) | His; Ura; Leu |

Inoculum 1 was inoculated from the glycerol stocks (100 μl) in 20 mL WMVIII medium in 100 mL shaking flask without baffles and incubated for 48 h at 30° C. and 150 rpm (amino acid supplementation listed in Table 7).

Inoculum 2 was inoculated from inoculum 1 (1%) in 20 mL WMVIII medium in 100 mL shaking flask without baffles and incubated for 48 h at 30° C. and 150 rpm (amino acid supplementation listed in table 7).

Inoculum 3 was inoculated from inoculum 2 (1%) in 50 mL WMVIII medium in 250 mL shaking flask with baffles and incubated for 48 h at 30° C. and 150 rpm (amino acid supplementation listed in table 7).

Inoculum 4 was inoculated from inoculum 3 (1%) in 50 mL WMVIII medium in 250 mL shaking flask with baffles and incubated for 48 h at 30° C. and 150 rpm (amino acid supplementation listed in table 7).

Inoculum 5 was inoculated from inoculum 4 (1%) in 50 mL WMVIII medium in 250 mL shaking flask with baffles and incubated for 48 h at 30° C. and 150 rpm (amino acid supplementation listed in table 7).

Inoculum 6 was inoculated from inoculum 5 (1%) in 50 mL WMVIII medium in 250 mL shaking flask with baffles and incubated for 48 h at 30° C. and 150 rpm (amino acid supplementation listed in table 7).

b.) Counting of Cells for Determination of Number of Generations:

TABLE 8

Number of cells per mL of culture (inoculum 1-6) at 0 hours (t = 0 h; after inoculation) and 48 hours (t = 48 h) of cultivation

| | Strain number | | | |
|---|---|---|---|---|
| | 1. | 2. | 3. | 4. |
| Inoculum 1, t = 48 h | $3.68 \times 10^8$ | $3.78 \times 10^8$ | $3.50 \times 10^8$ | $4.89 \times 10^8$ |
| Inoculum 2, t = 0 h | $6.38 \times 10^6$ | $6.38 \times 10^6$ | $6.50 \times 10^6$ | $7.63 \times 10^6$ |
| Inoculum 2, t = 48 h | $3.46 \times 10^8$ | $3.58 \times 10^8$ | $3.86 \times 10^8$ | $3.66 \times 10^8$ |
| Inoculum 3, t = 0 h | $8.13 \times 10^6$ | $9.00 \times 10^6$ | $9.75 \times 10^6$ | $10.38 \times 10^6$ |
| Inoculum 3, t = 48 h | $3.39 \times 10^8$ | $3.41 \times 10^8$ | $3.44 \times 10^8$ | $5.15 \times 10^8$ |
| Inoculum 4, t = 48 h | $3.03 \times 10^8$ | $3.04 \times 10^8$ | $2.99 \times 10^8$ | $3.87 \times 10^8$ |
| Inoculum 5, t = 48 h | $3.09 \times 10^8$ | $3.46 \times 10^8$ | $3.79 \times 10^8$ | $4.15 \times 10^8$ |
| Inoculum 6, t = 48 h | $5.61 \times 10^8$ | $5.39 \times 10^8$ | $5.74 \times 10^8$ | $6.73 \times 10^8$ |

Total Number of Generations:

Inoculums 1 to 5: approximately 5.5 generations

Inoculum 6: approximately 6.0 generations

Sum: approximately 33.5 generations c.) Preparation of Post-Production Glycerol Stocks:

The post-production glycerol stocks were prepared by mixing 0.5 mL of inoculum 6 after 48 hours of cultivation (of strains listed in table 7) with 0.5 mL glycerol solution (50% (v/v) glycerol in water).

TABLE 9

Denotation of glycerol stocks of post-production cells

| No. | Strain (Post-production stocks) | Phenotype | Supplements |
|---|---|---|---|
| 1. | AH22tH3ura8Δare1Δare2 post | auxotroph | His; Ura; Leu |
| 2. | AH22tH3ura8Δare1Δare2HUL post | prototroph | — |

The post-production glycerol stocks were stored at least 24 hours at −80° C. before cultivation for stability analysis.

4.2. Strain Stability (Prae and Post Production) Analysis a.) Cultivation Procedure Inoculum 1 was inoculated from the glycerol stocks (100 μl) listed in tables 7 and 3 (prae- and post production cells of 2 strains=4 stocks) in 20 mL WMVIII medium in 100 mL shaking flask without baffles and incubated for 48 h at 30° C. and 150 rpm (amino acid supplementation listed in table 7).

Inoculum 2 was inoculated from inoculum 1 (1%) in 50 mL WMVIII medium in 250 mL shaking flask with baffles and incubated for 72 h at 30° C. and 150 rpm (amino acid supplementation listed in table 7).

TABLE 10

Strains used for growth and squalene productivity analysis

| No. | Strain |
|---|---|
| 1. | AH22tH3ura8Δare1Δare2 prae (auxotrophic strain; prae stock) |
| 2. | AH22tH3ura8Δare1Δare2 post (auxotrophic strain; post stock) |
| 3. | AH22tH3ura8Δare1Δare2HUL prae (prototrophic strain; prae stock) |
| 4. | AH22tH3ura8Δare1Δare2HUL post (prototrophic strain; post stock) | b.) Results

After 72 hours the cells (inoculum 2) were harvested and evaluated concerning growth and productivity. For this purpose, the cell dry weight (CDW) was determined:

3×6 mL of culture broth was harvested in weighted 15 mL falcon tubes (triplicates) and pelleted via centrifugation at 4000 rpm, 5 min. The supernatant was discarded and the pellet used for further analysis. The pellets are washed 2 times with 5 mL of water. The washed pellets were dried at 80° C. for 24 h and cooled in an exicator before weighing.

The determination of the cell dry weight (CDW) was carried out in triplicates and extraction and squalene analysis was carried out in triplicates.

The measurement of the optical density at 600 nm ($OD600_{nm}$) of the strains depicted in Table 10 shows that the prototrophic AH22tH3ura8Δare1Δare2HUL strain was more stable than the auxotrophic AH22tH3ura8Δare 1Δare2 strain. After 72 h, the following results were obtained:

TABLE 11 growth of strains after incubation

| No. | Strain | Optical density at 600 nm ($OD600_{nm}$)/mL |
|---|---|---|
| 1. | AH22tH3ura8Δare1Δare2 prae | 58 |
| 2. | AH22tH3ura8Δare1Δare2 post | 51 |
| 3. | AH22tH3ura8Δare1Δare2HUL prae | 58 |
| 4. | AH22tH3ura8Δare1Δare2HUL post | 59 |

The measurement of the cell dry weight (CDW) of the strains listed in Table 10 shows that the prototrophic AH22tH3ura8Δare1Δare2HUL strain was more stable than the auxotrophic AH22tH3ura8Δare1Δare2 strain. After 72 h, the following results were obtained:

TABLE 12 cell dry weight (CDW) after incubation

| No. | Strain | Cell dry weight [g/L] |
|---|---|---|
| 1. | AH22tH3ura8Δare1Δare2 prae | 12.4 |
| 2. | AH22tH3ura8Δare1Δare2 post | 10.2 |
| 3. | AH22tH3ura8Δare1Δare2HUL prae | 13.0 |
| 4. | AH22tH3ura8Δare1Δare2HUL post | 13.1 |

The measurement of the squalene productivity of the strains listed in Table 10 shows that the prototrophic AH22tH3ura8Δare1Δare2HUL strain was more stable than the auxotrophic AH22tH3ura8Δare1Δare2 strain and produces larger amounts of squalene. After 72 h, the following results were obtained:

TABLE 13 cell dry weight (CDW) after incubation

| No. | Strain | Squalene [g/L culture broth] | Squalene [% per cell dry weight] |
|---|---|---|---|
| 1. | AH22tH3ura8Δare1Δare2 prae | 0.68 | 5.48 |
| 2. | AH22tH3ura8Δare1Δare2 post | 0.49 | 4.81 |
| 3. | AH22tH3ura8Δare1Δare2HUL prae | 0.90 | 6.97 |
| 4. | AH22tH3ura8Δare1Δare2HUL post | 0.88 | 6.84 |

4.3 Conclusions

The prototrophic strain AH22tH3ura8Δare1Δare2HUL produced more squalene in comparison to the auxotrophic strain AH22tH3ura8Δare1Δare2 concerning the volumetric, the specific and the total yield. Further, the cell dry weight of the prototrophic strain at the end of the cultivation was higher compared to the auxotrophic strain. In contrast to the auxotrophic strain, the prototrophic strain was stable concerning growth performance and squalene productivity over at least 33 generations.

Example 5

Evaluation of AH22tH3ura8Δare1Δare2HUL 5.1. Lab-Scale Fermentation of AH22tH3Ura8Δare1Δare2HUL
Strain: *Saccharomyces cerevisiae* AH22tH3ura8Δare1Δare2HUL
Medium: sterilized WMVIII basic medium (20 min/121° C.) supplemented with sterile filtrated (0.22 μm) trace elements and vitamins
Precultivation:
Inoculum 1: 20 mL WMVIII—medium (100 mL Erlenmeyer flask with baffles) inoculated with 20 μl of glycerol stock of strain AH22tH3ura8Δare1Δare2HUL
Incubation: 48 h/30° C./150 rpm
Inoculum 2: 150 mL WMVIII—medium (500 mL Erlenmeyer flask with baffles) inoculated with 1.5 mL (1%) Inoculum 1
Incubation: 48 h/30° C./150 rpm
Main Cultivation:
3 L WMVIII—medium (5 L Applikon fermenter) inoculated with 100 mL (3.33%) Inoculum 2 and incubated for 72 h at 30° C. and 250-585 rpm. There was no pH control. The incubator was vented with 10 L/h compressed air.
Agitation: $pO_2$-controlled (if the $pO_2$ value was less than 25% the agitation was successively increased up to a maximum of 700 rpm)

Figure 7A:
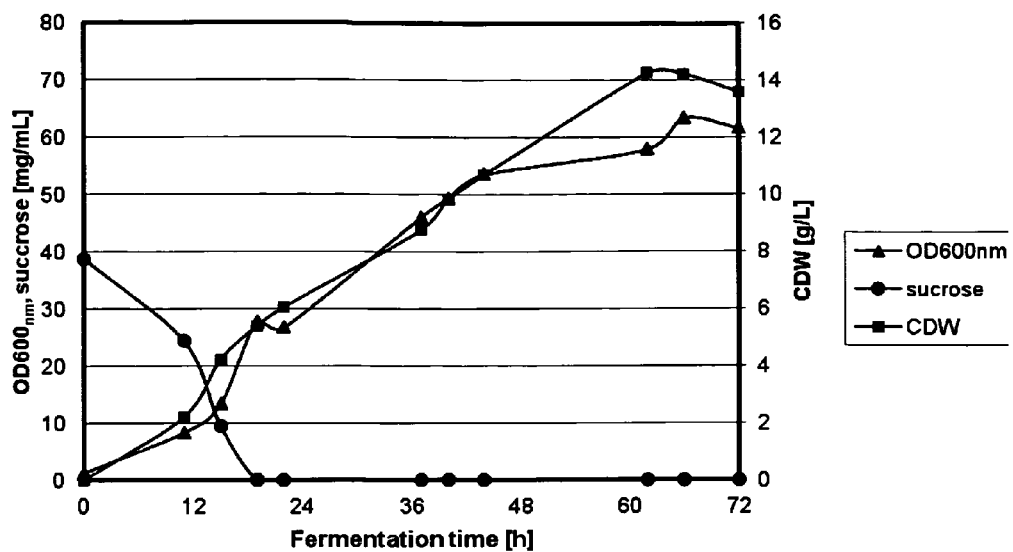
FIG. 7A shows the growth of the yeasts over time. Cell dry weight (CDW) in g/L and the optical density ($OD_{600nm}$/mL) in the course of the fermentation is depicted.
Figure 7B:
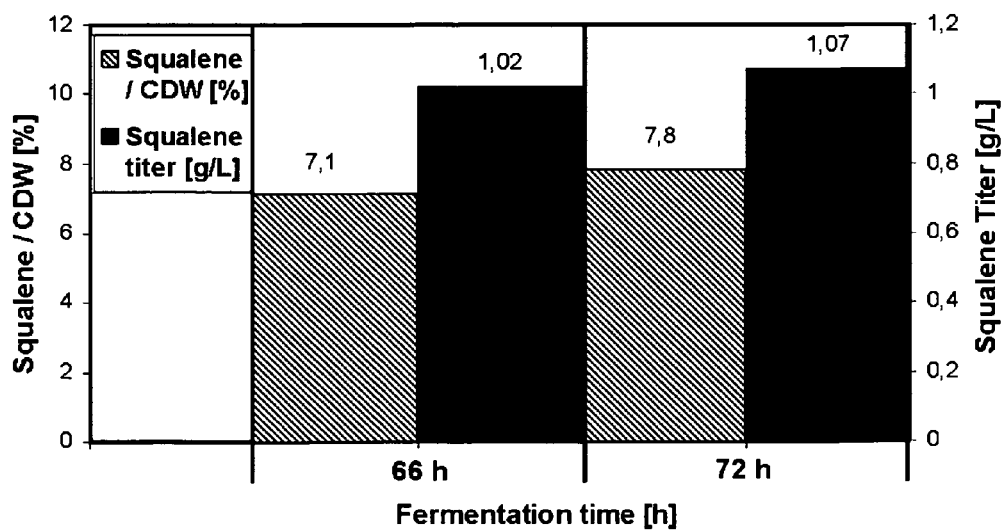
FIG. 7B shows the squalene productivity after 66 h and 72 h. Squalene productions is depicted in percent per cell dry weight and volumetric productivity in g/L of fermentation broth in the course of the fermentation.

Fermentation
The AH22tH3ura8Δare1Δare2HUL cells were fermented in calendar week 39 (2010).
Recorded Parameters: pH and $pO_2$ at the Beginning of Incubation
start: 0 h
pH: 5.24
$pO_2$: 99%
stirring rate: 250 rpm
ventilation: 10 L/h compressed air
During incubation samples for chemical analysis and optical density measurements were analyzed. Sampling timed were after 0 h, 11 h, 15 h, 19 h, 22 h, 37 h, 40 h, 44 h, 62 h, 66 h, 1nd 72 h.
recorded parameters: pH and $pO_2$ at the end of incubation
end: 72 h
pH: 5.26
$pO_2$: 59%
stirring rate: 250 rpm
ventilation: 10 L/h compressed air
Results
The results are depicted in FIG. 7. The growth kinetic was extensively linear for more than 60 h of incubation. Squalene productivity of the culture increased up to 60 h. The squalene productivity was 1.07 g $L^{-1}$ (titer) respectively 7.8% (squalene per CDW) after 72 hours of fermentation time.

REFERENCES

EP 0 486 290 A2

Basson M E, Thorsness M, Finer-Moore J, Stroud R M, Rine J (1988); Structural and functional conservation between yeast and human 3-hydroxy-3-methylglutaryl coenzyme A reductases, the rate-limiting enzyme of sterol biosynthesis; Mol. Cell. Biol. 8:3797-3808.

Bennetzen J L, Hall B D (1982); The primary structure of the *Saccharomyces cerevisiae* gene for alcohol dehydrogenase; J Biol. Chem. 257:3018-3025.

Berben G, Dumont J, Gilliquet V, Bolle P A, Hilger F (1991); The YDp plasmids: a uniform set of vectors bearing versatile gene disruption cassettes for *Saccharomyces cerevisiae*; Yeast. 7:475-477.

Boeke J D, Trueheart J, Natsoulis G, Fink G R (1987); 5-Fluoroorotic acid as a selective agent in yeast molecular genetics; Methods Enzymol. 154:164-175.

Gaber R F, Culbertson M R (1982); Frameshift suppression in *Saccharomyces cerevisiae*. IV. New suppressors among spontaneous co-revertants of the Group II his4-206 and leu 2-3 frameshift mutations; Genetics 101:345-367.

Gietz D, St Jean A, Woods R A, Schiestl R H (1992); Improved method for high efficiency transformation of intact yeast cells; Nucleic Acids Res. 20:1425.

Guldener U, Heck S, Fielder T, Beinhauer J, Hegemann J H (1996); A new efficient gene disruption cassette for repeated use in budding yeast. Nucleic Acids Res. 24:2519-24.

Hinnen A, Hicks J B, Fink G R (1978); Transformation of yeast. Proc Natl Acad Sci USA. 75:1929-1933.

Lang C and Looman A C (1995); Efficient expression and secretion of *Aspergillus niger RH*5344 polygalacturonase in *Saccharomyces cerevisiae*; Appl Microbiol Biotechnol 44:147-156.

Mortimer R K, Johnston J R (1986); Genealogy of principal strains of the yeast genetic stock center; Genetics 113:35-43.

Parent S A, Fenimore C M, Bostian K A (1985); Vector systems for the expression, analysis and cloning of DNA sequences in *S. cerevisiae*; Yeast 1:83-138.

Polakowski T, Stahl U, Lang C (1998); Overexpression of a cytosolic hydroxymethylglutaryl-CoA reductase leads to squalene accumulation in yeast; Appl Microbiol Biotechnol. 49:66-71.

Pronk J T (2002); Auxotrophic yeast strains in fundamental and applied research; Appl Environ Microbiol. 68:2095-2100.

Tschumper G, Carbon J (1980); Sequence of a yeast DNA fragment containing a chromosomal replicator and the TRP1 gene; Gene 10:157-166.

Webster T D, Dickson R C (1983); Direct selection of *Saccharomyces cerevisiae* resistant to the antibiotic G418 following transformation with a DNA vector carrying the kanamycin-resistance gene of Tn903; Gene 26:243-252.

Yanisch-Perron C, Vieira J, Messing J (1985); Improved M13 phage cloning vectors and host strains: nucleotide sequences of the M13 mp 18 and pUC19 vectors; Gene 33:103-119. Erratum in Gene 114:81-83.

The invention claimed is:

1. A yeast cell, wherein
   a) said cell comprises a functional gene coding for soluble hydroxymethylglutaryl-coenzyme-A (HMG-CoA) reductase;
   b) one or more gene(s) coding for steryl acyltransferase(s) in said cell are defective or deleted; and
   c) said cell is prototrophic for histidine, leucine and uracil.

2. The cell according to claim 1, wherein said cell is a cell of a stable cell line.

3. The cell according to claim 1, wherein said cell is a genetically modified cell.

4. The cell according to claim 1, wherein said cell is a *Saccharomyces cerevisiae* cell of the strain AH22.

5. The cell according to claim 1, wherein the soluble HMG-CoA reductase is characterized in that
   a) it is a truncated soluble HMG-CoA reductase protein lacking the membrane-binding region;
   b) it is encoded on a vector under the transcriptional control of a promoter that is active in said cell; and/or
   c) it is expressed under the control of a constitutive promoter.

6. The cell according to claim 1, wherein the one or more gene(s) coding for steryl acyltransferase(s) are ARE1 and ARE2.

7. The cell according to claim 1, wherein the terpene productivity of said cell is at least equivalent in comparison with the corresponding wildtype cell.

8. The cell according to claim 1, wherein said cell produces reduced amounts of steryl acyl esters.

9. The cell according to claim 1, wherein the terpene productivity of said cell is at least equivalent in comparison with the corresponding cell which is auxotrophic for at least one of histidine, leucine, or uracil.

10. A method of generating a modified yeast cell, said method comprising:
    a) inserting a gene coding for soluble HMG-CoA reductase into a yeast cell;
    b) selecting cells comprising a gene coding for said soluble HMG-CoA reductase;
    c) deleting or mutating one or more gene(s) coding for steryl acyltransferase(s) of said cell;
    d) converting said cell into a cell that is at least prototrophic for histidine, leucine and uracil, by means of
       (i) inserting gene cassette(s) coding for one or more enzyme(s) for the production of histidine, leucine and/or uracil, and
       (ii) revertant mutagenesis of one or more defective gene(s) coding for enzymes for the production of histidine, leucine or uracil, and
    e) selecting cells that are prototrophic for histidine, leucine and uracil.

11. The method according to claim 10, wherein said cell is derived from a *Saccharomyces cerevisiae* cell of the strain AH22.

12. The method according to claim 10, wherein step a) comprises the insertion of a vector coding for soluble HMG-CoA reductase, wherein the expression of said soluble HMG-CoA reductase is under the control of a strong constitutive promoter active in said cell.

13. The method according to claim 10, wherein the one or more gene(s) coding for steryl acyltransferase(s) are ARE1 and ARE2.

14. A method for the production of squalene, said method comprising:
    a) cultivating the cells of claim 1 in a suitable culture medium; and
    b) isolating squalene from the cells.

15. A method for the production of a pharmaceutical composition, said method comprising:
    a) producing squalene by cultivating the cells of claim 1 in a suitable culture medium
    b) isolating squalene from the cells, and
    c) admixing squalene to said pharmaceutical composition.

16. The method according to claim 10, wherein step d) is performed by revertant mutagenesis of a defective gene coding for an enzyme for the production of histidine and by inserting gene cassettes coding for enzymes for the production of leucine and uracil.

* * * * *